United States Patent
Tato et al.

(10) Patent No.: US 8,691,227 B2
(45) Date of Patent: Apr. 8, 2014

(54) METHODS OF TREATING MULTIPLE SCLEROSIS, RHEUMATOID ARTHRITIS AND INFLAMMATORY BOWEL DISEASE USING AGONISTS ANTIBODIES TO PILR-α

(75) Inventors: Cristina M. Tato, Menlo Park, CA (US); Barbara Joyce-Shaikh, San Jose, CA (US); Daniel J. Cua, Palo Alto, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/516,635

(22) PCT Filed: Dec. 10, 2010

(86) PCT No.: PCT/US2010/059893
§ 371 (c)(1),
(2), (4) Date: Dec. 3, 2012

(87) PCT Pub. No.: WO2011/084357
PCT Pub. Date: Jul. 14, 2011

(65) Prior Publication Data
US 2013/0071380 A1 Mar. 21, 2013

Related U.S. Application Data

(60) Provisional application No. 61/287,584, filed on Dec. 17, 2009.

(51) Int. Cl.
*A61K 39/00* (2006.01)

(52) U.S. Cl.
USPC .................................. 424/133.1; 424/139.1

(58) Field of Classification Search
None
See application file for complete search history.

(56) References Cited

U.S. PATENT DOCUMENTS

| | | |
|---|---|---|
| 2003/0223991 A1 | 12/2003 | Cherwinski et al. |
| 2006/0177436 A1 | 8/2006 | Ghilardi et al. |
| 2009/0162350 A1* | 6/2009 | Abbas et al. ............... 424/133.1 |

FOREIGN PATENT DOCUMENTS

| | | |
|---|---|---|
| EP | 2127672 | 12/2009 |
| WO | WO 98/24906 | 6/1998 |
| WO | WO 00/40721 | 7/2000 |
| WO | WO 2005/051220 | 6/2005 |
| WO | WO 2007/099921 | 9/2007 |
| WO | WO 2008/025031 | 2/2008 |
| WO | WO 2008/025033 | 2/2008 |
| WO | WO 2008/070097 | 6/2008 |

OTHER PUBLICATIONS

Amadi-Obi et al. (2007) *Nat. Med.* 13(6):711-718 "TH17 cells contribute to uveitis and scleritis and are expanded by IL-2 and inhibited by IL-27/STAT1".

Artis, et al. (2004) *J Immunol* 173(9):5626-5634 "The IL-27 receptor (WSX-1) is an inhibitor of innate and adaptive elements of type 2 immunity".

Banerjee et al. (2010) *Infect Immun.* 78(3):1353-1363 "Modulation of paired immunoglobulin-like type 2 receptor signaling alters the hose response to *Staphylococcus aureas*-induced pneumonia".

Bixel, et al. (2007) *Blood* 109:5327-5336 "A CD99-related antigen on endothelial cells mediates neutrophil but not lymphocyte extravasation in vivo".

Cherwinski, et al. (2005) *J. Immunol.* 174:1348 "The CD200 Receptor Is a Novel and Potent Regulator of Murine and Human Mast Cell Function[1]".

Collison and Vignali (2008) *Immunol Rev.* 226:248-262 "Interleukin-35: odd one out or part of the family?"

Cosmi, et al. (2006) *Clin. Exp. Allergy* 36(3):261-272 "Sublingual immunotherapy with *Dermatophagoides* monomeric allergoid down-regulates allergen-specific immunoglobulin E and increases both interferon-gamma- and interleukin-10-production".

Diveu, et al. (2008) *Curr. Op. Immunol.* 20(6):663-668 "Cytokines that regulate autoimmunity".

Diveu, et al. (2009) *J Immunol* 182(9):5748-5756 "IL-27 blocks RORc expression to inhibit lineage commitment of Th17 cells".

Dufour, et al. (2008) *Cell Commun Adhes.* 15(4):351-363 "CD99 is essential for leukocyte diapedesis in vivo".

Fitzgerald & Rostami (2009) *Expert Opin. Biol. Ther.* 9(2):149-160 "Therapeutic potential of IL-27 in multiple sclerosis?"

Fitzgerald, et al. (2007) *J Immunol* 179(5):3268-3275 "Suppressive effect of IL-27 on encephalitogenic Th17 cells and the effector phase of experimental autoimmune encephalomyelitis".

Fitzgerald, et al. (2007) *Nat Immunol* 8(12):1372-1379 "Suppression of autoimmune inflammation of the central nervous system by interleukin 10 secreted by interleukin 27-stimulated T cells".

Fournier, et al. (2000) *J Immunol* 165:1197-1209 "FDF03, a novel inhibitory receptor of the immunoglobulin superfamily, is expressed by human dendritic and myeloid cells".

Furuzawa-Carballeda, et al. (2007) *Autoimmun Rev* 6:169-175 "Autoimmune inflammation from the Th17 perspective".

Goriely et al. (2009) *Allergy* 64(5):702-709 "Interleukin-12 family members and type I interferons in Th17-mediated inflammatory disorders".

Ilarregui, et al. (2009) Nat Immunol 10:981-991 "Tolerogenic signals delivered by dendritic cells to T cells through a galectin-1-driven immunoregulatory circuit involving interleukin 27 and interleukin 10".

Jankovic, et al. (2007) *J Exp Med* 204(2):273-283 Conventional T-bet(+)Foxp3(−) Th1 cells are the major source of host-protective regulatory IL-10 during intracellular protozoan infection.

Li, et al. (2005) *J Neurol Sci* 232:3-9 "IL-27 subunits and its receptor (WSX-1) mRNAs are markedly up-regulated in inflammatory cells in the CNS during experimental autoimmune encephalomyelitis".

Liesenfeld (2002) *J Infect Dis* 185 Suppl 1:S96-101 Oral infection of C57BL/6 mice with *Toxoplasma gondii*: a new model of inflammatory bowel disease?

(Continued)

*Primary Examiner* — Robert Landsman
(74) *Attorney, Agent, or Firm* — Gregory R. Bellomy

(57) ABSTRACT

The present invention provides methods of using PILRα agonists, or PILRβ antagonists, to treat immune disorders, such as autoimmune and inflammatory disorders, including CNS, joint and gut inflammation.

6 Claims, 19 Drawing Sheets

(56) References Cited

OTHER PUBLICATIONS

Liesenfeld, et al. (1999) *Parasite Immunol* 21:365-376 "TNF-alpha, nitric oxide and IFN-gamma are all critical for development of necrosis in the small intestine and early mortality in genetically susceptible mice infected perorally with *Toxoplasma gondii*".
Liesenfeld, et al. (1996) *J Exp Med* 184:597-607 "Association of CD4+ T cell-dependent, interferon-gamma-mediated necrosis of the small intestine with genetic susceptibility of mice to peroral infection with *Toxoplasma gondii*".
Lou, et al. (2007) *J Immunol* 178(2):1136-1143 "CD99 is a key mediator of the transendothelial migration of neutrophils".
Mascarell et al. (2008) *J. Allergy Clin. Immunol.* 122(3):603-609 "Oral dendritic cells mediate antigen-specific tolerance by stimulating TH1 and regulatory CD4+ T cells".
Mousseau, et al. (2000) *J Biol Chem* 275:4467-4474 "PILRalpha, a novel immunoreceptor tyrosine-based inhibitory motif-bearing protein, recruits SHP-1 upon tyrosine phosphorylation and is paired with the truncated counterpart PILRbeta."
Murugaiyan, et al. (2009) *J Immunol* 183:2435-2443 "IL-27 is a key regulator of IL-10 and IL-17 production by human CD4+ T cells".
Niedbala, et al. (2008) *Ann Rheum Dis* 67:1474-1479 "Interleukin 27 attenuates collagen-induced arthritis".
Oh, et al. (2007) *Exp Mol Med* 39(2):176-184 "CD99 activates T cells via a costimulatory function that promotes raft association of TCR complex and tyrosine phosphorylation of TCR zeta".
Satoh and Arase (2008) *Uirusu* 58:27-36. (JP version) "HSV-1 infection through inhibitory receptor, PILRalpha".
Satoh, et al. (2008) *Cell* 132:935-944 "PILRalpha is a herpes simplex virus-1 entry coreceptor that associates with glycoprotein B".
Shiratori, I., K. Ogasawara, T. Saito, L.L. Lanier, and H. Arase. 2004. Activation of natural killer cells and dendritic cells upon recognition of a novel CD99-like ligand by paired immunoglobulin-like type 2 receptor. J Exp Med 199:525-533.
Sonobe, et al. (2005) *Brain Res* 1040:202-207 "Production of IL-27 and other IL-12 family cytokines by microglia and their subpopulations".
Stock et al. (2004) *Nat. Immunol.* 5(11):1149-1156 "Induction of T helper type 1-like regulatory cells that express Foxp3 and protect against airway hyper-reactivity".
Stumhofer, et al. (2006) *Nat Immunol* 7(9):937-945 "Interleukin 27 negatively regulates the development of interleukin 17-producing T helper cells during chronic inflammation of the central nervous system".
Stumhofer and Hunter (2008) *Immunol Lett* 117:123-130 "Advances in understanding the anti-inflammatory properties of IL-27".
Stumhofer, et al. (2007) *Nat Immunol* 8:1363-1371 "Interleukins 27 and 6 induce STAT3-mediated T cell production of interleukin 10".
Sugiyama et al. (2008) *Ann. Rheum. Dis.* 67(10):1461-1467 "Amelioration of human lupus-like phenotypes in MRL/lpr mice by overexpression of interleukin 27 receptor alpha (WSX-1)".
Tabata, et al. (2008) *J Biol Chem* 283:8893-8901 "Biophysical characterization of O-glycosylated CD99 recognition by paired Ig-like type 2 receptors".
Tait and Hunter (2009) *Mem Inst Oswaldo Cruz* 104:201-210 "Advances in understanding immunity to *Toxoplasma gondii*".
Troy, et al. (2009) *J Immunol* 183:2037-2044 "IL-27 regulates homeostasis of the intestinal CD4+ effector T cell pool and limits intestinal inflammation in a murine model of colitis".
Turnbull and Colonna (2007) *Nat Rev Immunol* 7:155-161 "Activating and inhibitory functions of DAP12".
Villarino, et al. (2003) *Immunity* 19:645-655 "The IL-27R (WSX-1) is required to suppress T cell hyperactivity during infection".
Villarino, et al. (2006) *J Immunol* 176:237-247 "IL-27 limits IL-2 production during Th1 differentiation".
Wang et al. (2008) *J Immunol* 180(3):1686-1693 "An essential role of sialylated O-linked sugar chains in the recognition of mouse CD99 by paired Ig-like type 2 receptor (PILR)".
Wright et al. (2003) *J. Immunol.* 171:3034-3046 "Characterization of the CD200 Receptor Family in Mice and Humans and Their Interactions with CD200".
Zhang et al. (2004) *J. Immunol.* 173:6786-6793 "Molecular Mechanisms of CD200 Inhibition of Mast Cell Activation".

\* cited by examiner

SEQUENCE LISTING

```
<160> NUMBER OF SEQ ID NOS: 8

<210> SEQ ID NO 1
<211> LENGTH: 1323
<212> TYPE: DNA
<213> ORGANISM: Homo sapiens
<220> FEATURE:
<221> NAME/KEY: sig_peptide
<222> LOCATION: (213)..(269)

<400> SEQUENCE: 1 aatagggggaa aataagccag atggataaag gaagtgctgg tcaccctgga ggtgcactgg      60
tttggggaag gctcctggcc cccacagccc tcttcggagc ctgagcccgg ctctcctcac     120
tcacctcaac cccaggcgg ccctccaca gggcccctct cctgcctgga cggctctgct     180
ggtctccccg tcccctggag aagaacaagg ccatgggtcg gcccctgctg ctgccctac     240 tgcccttgct gctgccgcca gcatttctgc agcctagtgg ctccacagga tctggtccaa     300
```

-continued

```
gctacccttta tggggtcact caaccaaaac acctctcagc ctccatgggt ggctctgtgg    360 aaatccccctt ctccttctat taccccctggg agttagccac agctcccgac gtgagaatat    420
cctggagacg gggccacttc cacaggcagt ccttctacag cacaaggccg ccttccattc    480
acaaggatta tgtgaaccgg ctctttctga actggacaga gggtcagaag agcggcttcc    540
tcaggatctc caacctgcag aagcaggacc agtctgtgta tttctgccga gttgagctgg    600
acacacggag ctcagggagg cagcagtggc agtccatcga ggggaccaaa ctctccatca    660
cccaggctgt cacgaccacc acccagaggc ccagcagcat gactaccacc tggaggctca    720
gtagcacaac caccacaacc ggcctcaggg tcacacaggg caaacgacgc tcagactctt    780
ggcacataag tctggagact gctgtggggg tggcagtggc tgtcactgtg ctcggaatca    840
tgattttggg actgatctgc ctcctcaggt ggaggagaag gaaaggtcag cagcggacta    900
aagccacaac cccagccagg gaaccccttcc aaaacacaga ggagccatat gagaatatca    960
ggaatgaagg acaaaataca gatcccaagc taaatcccaa ggatgacggc atcgtctatg   1020
cttcccttgc cctctccagc tccacctcac ccagagcacc tcccagccac cgtcccctca   1080 agagcccccca gaacgagacc ctgtactctg tcttaaaggc ctaaccaatg gacagccctc   1140
tcaagactga atggtgaggc caggtacagt ggcgcacacc tgtaatccca gctactctga   1200
agcctgaggc agaatcaagt gagcccagga gttcagggcc agctttgata atggagcgag   1260
atgccatctc tagttaaaaa tatatattaa caataaagta acaaatttaa aaagataaaa   1320
aaa                                                                 1323
```

<210> SEQ ID NO 2
<211> LENGTH: 303
<212> TYPE: PRT
<213> ORGANISM: Homo sapiens
<220> FEATURE:
<221> NAME/KEY: SIGNAL
<222> LOCATION: (1)..(19)
<220> FEATURE:
<221> NAME/KEY: mat_peptide
<222> LOCATION: (20)..(303)

<400> SEQUENCE: 2

```
Met Gly Arg Pro Leu Leu Leu Pro Leu Leu Pro Leu Leu Pro Pro
             -15                 -10                  -5

Ala Phe Leu Gln Pro Ser Gly Ser Thr Gly Ser Gly Pro Ser Tyr Leu
    -1   1               5                  10

Tyr Gly Val Thr Gln Pro Lys His Leu Ser Ala Ser Met Gly Gly Ser
         15                  20                  25

Val Glu Ile Pro Phe Ser Phe Tyr Tyr Pro Trp Glu Leu Ala Thr Ala
 30                  35                  40                  45

Pro Asp Val Arg Ile Ser Trp Arg Arg Gly His Phe His Arg Gln Ser
                 50                  55                  60

Phe Tyr Ser Thr Arg Pro Pro Ser Ile His Lys Asp Tyr Val Asn Arg
             65                  70                  75

Leu Phe Leu Asn Trp Thr Glu Gly Gln Lys Ser Gly Phe Leu Arg Ile
         80                  85                  90

Ser Asn Leu Gln Lys Gln Asp Gln Ser Val Tyr Phe Cys Arg Val Glu
     95                 100                 105

Leu Asp Thr Arg Ser Ser Gly Arg Gln Gln Trp Gln Ser Ile Glu Gly
110                 115                 120                 125

Thr Lys Leu Ser Ile Thr Gln Ala Val Thr Thr Thr Gln Arg Pro
                130                 135                 140
```

```
Ser Ser Met Thr Thr Thr Trp Arg Leu Ser Ser Thr Thr Thr Thr Thr
            145                 150                 155
Gly Leu Arg Val Thr Gln Gly Lys Arg Arg Ser Asp Ser Trp His Ile
        160                 165                 170
Ser Leu Glu Thr Ala Val Gly Val Ala Val Ala Val Thr Val Leu Gly
    175                 180                 185
Ile Met Ile Leu Gly Leu Ile Cys Leu Leu Arg Trp Arg Arg Arg Lys
190                 195                 200                 205
Gly Gln Gln Arg Thr Lys Ala Thr Thr Pro Ala Arg Glu Pro Phe Gln
                210                 215                 220
Asn Thr Glu Glu Pro Tyr Glu Asn Ile Arg Asn Glu Gly Gln Asn Thr
            225                 230                 235
Asp Pro Lys Leu Asn Pro Lys Asp Asp Gly Ile Val Tyr Ala Ser Leu
        240                 245                 250
Ala Leu Ser Ser Ser Thr Ser Pro Arg Ala Pro Pro Ser His Arg Pro
    255                 260                 265
Leu Lys Ser Pro Gln Asn Glu Thr Leu Tyr Ser Val Leu Lys Ala
270                 275                 280
```

<210> SEQ ID NO 3
<211> LENGTH: 3632
<212> TYPE: DNA
<213> ORGANISM: Homo sapiens
<220> FEATURE:
<221> NAME/KEY: sig_peptide
<222> LOCATION: (2497)..(2553)

<400> SEQUENCE: 3

```
agaagggagg tagtcgccct ccgtcgtggc ctggcgtgga ttccgagcgt tggtgtctgg    60
cggtttccga ccgttggtgt ctggcacgcg ccaccccgat gtaccaggta aagccctatc   120
acggggtcgg cgcccctctc cgtgtggagc ccacctgcat gtactggctc cccaacatgc   180
acggcaggag cggcggccca gcactcggca ctggccactt gcagacaaga agacaagaaa   240
atgatttgag acagcttca atcgcggtgt gaagaagaaa gcaacaaaac gaccactgaa    300
aacaatgccg gtggcaaaac atccaaagaa agggtcccaa gtggtacatc gtcatagctg   360
gaaacagtca gagccaccag ccaatgatct tttcaatgct gcgaaagctg ccaaaagtga   420
catgcagtgt ggccatgagg tctgccggaa gtgacttgtt ggtgttatct cctgagttaa   480
aatgtgaagg gatttttttt tttcagatta ctgagagtct tcagttacta gaggcggatt   540
tccctgactg aagaccatgt tgcaggccca cagctgccta cagaaccgtc ccaaaatatg   600
gcaaagaaac ctattctgag cgatagggtc tcaccatgtt gcccaggctg gtcttgaact   660
cctggactca tcctaaagtg ctggcctctc attccctgtc tgtgcacacc tcacggcaag   720
ggccagcctg tttcctcccg gtcacctcca atcttgctg cttttaattc aactcagagg    780
cctagccagg gttgagttct cacccacctg tgccgccctg ccttgttacc tggaagcaca   840
gccttgggga ctgagcaggc cctcactgtc actttaagaa gggaatcagc cactttgtgc   900
tcaccacctc tggggaaggt gtgagaggag agaaggaagt ggctgtttgg ctgctgacaa   960
catgaagact tcctgcgatg agaacagagg cacaggtgcc ggccctgcag ccccagaac   1020
ccggactgga gggggccatg gggcgccgga ccctggccct gccctgggtg ctgctgaccc  1080
tgcgtgtcac tgcagggacc ccggaggtgt gagtacaagt tcggatggag gccaccgagc  1140
tctcgtcctt caccatccgt gtgggttcc tggagtctgg ctccatctcc ctggtgactg   1200
cccgctggga aacccagagc agcatctctc tcatcctgga aggctctggg gccagcagcc  1260
```

```
cctgcgccaa caccaccttc tgctgcaagt ttgcgtcctt ccctgagggc tcctgggagg    1320
cctgtgggag cctcccgccc agctcagacc cagggctctc tgtcccgccg actcctgccc    1380
ccattctgcg ggcagacctg ccgggatct tggggggtctc aggagtcctt ctctttgact    1440
gtggctacct ccttcatctg ctgtgccgac agaagcaccg ccctgcccct aggctccagc    1500
catcccacac cagctcctag gcactgagag cacgagcatg ggcacccagc caggcctccc    1560
aggctgctct ccacgtccct tatgccacta tcaacaccag ctgctgccca gctactttgg    1620
acacagctca cccccgacag ggggccgtcc tggtgggcat cactccccac ccacaccgca    1680
cactggcccc agggccctgc tgcctgggcc tccacatcca tccctgcaca tggcagcttt    1740
gtctctgttg agaatggact ctacgcttag gctgggcaga ggcctccctg cactggtcct    1800
ggcctcactc ttttccctga cccttgggggc ccagggccat ggagggaccc ttaggagttc    1860
aatgagagag accatgaggc cactgggctt tccccttccc aggcctcctg ggtgccaccc    1920
ccttacgtta ttcttgggcc tctaataagt gtcccacagg tgcctggcca ggcccacctg    1980
ctgcagatgt ggtctgtgtg tgtgcatgtg tgggtgtgtg tgggcacagg tgtgagtgtg    2040
tgagcaacag tacccccattc cagtcgtttc ctgctgtgac taagtcagca acacagttcc    2100
tctgacatgg gccttggctg tgcttctttg ggggtgaaga gattggggag gaagtctcca    2160
cccctgggag gcagaagcca ggcatagcgc gctggctagg actccagtac cgtgaaggga    2220
ggcagtgaga gcagacatct gtgcctcatt cctgatctca aggggaaagc aagaacaagg    2280
gaggcttcct caggatctcg aacctgcgga aggaggacca gtctgtgtac ttctgccaag    2340
tccagctgga catacagatc agggaggctg tcgtggcagt ccatcaaggg gacccacctc    2400
accatcaccc aggccctcag gcagcccctc cacagggccc ctctcctgcc tggacagctc    2460
tgctggtctc cccgtcccct ggagaagaac aaggccatgg gtcggcccct gctgctgccc    2520
ctgctgctcc tgctgcagcc gccagcattt ctgcagcctg gtggctccac aggatctggt    2580
ccaagctacc tttatggggt cactcaacca aaacacctct cagcctccat gggtggctct    2640
gtggaaatcc ccttctcctt ctattacccc tgggagttag ccatagttcc caacgtgaga    2700
atatcctgga gacggggcca cttccacggg cagtccttct acagcacaag gccgccttcc    2760
attcacaagg attatgtgaa ccggctctttt ctgaactgga cagagggtca ggagagcggc    2820
ttcctcagga tctcaaacct gcggaaggag gaccagtctg tgtatttctg ccagtcgag    2880 ctggacaccc ggagatcagg gaggcagcag ttgcagtcca tcaaggggac caaactcacc    2940
atcacccagg ctgtcacaac caccaccacc tggaggccca gcagcacaac caccatagcc    3000
ggcctcaggg tcacagaaag caaagggcac tcagaatcat ggcacctaag tctggacact    3060
gccatcaggg ttgcattggc tgtcgctgtg ctcaaaactg tcattttggg actgctgtgc    3120
ctcctcctcc tgtggtggag gagaaggaaa ggtagcaggg cgccaagcag tgacttctga    3180
ccaacagagt gtggggagaa gggatgtgta ttagccccgg aggacgtgat gtgagacccg    3240
cttgtgagtc ctccacactc gttccccatt ggcaagatac atggagagca ccctgaggac    3300
ctttaaaagg caaagccgca aggcagaagg aggctgggtc cctgaatcac cgactggagg    3360
agagttacct acaagagcct tcatccagga gcatccacac tgcaatgata taggaatgag    3420
gtctgaactc cactgaatta aaccactggc atttgggggc tgtttattat agcagtgcaa    3480
agagttcctt tatcctcccc aaggatggaa aaatacaatt tattttgctt accatacacc    3540 cctttttctcc tcgtccacat tttccaatct gtatggtggc tgtcttctat ggcagaaggt    3600 tttgggggaat aaatagcgtg aaatgctgct ga                                 3632
```

-continued

```
<210> SEQ ID NO 4
<211> LENGTH: 227
<212> TYPE: PRT
<213> ORGANISM: Homo sapiens
<220> FEATURE:
<221> NAME/KEY: SIGNAL
<222> LOCATION: (1)..(19)
<220> FEATURE:
<221> NAME/KEY: mat_peptide
<222> LOCATION: (20)..(227)

<400> SEQUENCE: 4

Met Gly Arg Pro Leu Leu Leu Pro Leu Leu Leu Leu Gln Pro Pro
                -15                 -10                  -5

Ala Phe Leu Gln Pro Gly Gly Ser Thr Gly Ser Gly Pro Ser Tyr Leu
    -1   1               5                   10

Tyr Gly Val Thr Gln Pro Lys His Leu Ser Ala Ser Met Gly Gly Ser
     15                  20                  25

Val Glu Ile Pro Phe Ser Phe Tyr Tyr Pro Trp Glu Leu Ala Ile Val
 30                  35                  40                  45

Pro Asn Val Arg Ile Ser Trp Arg Arg Gly His Phe His Gly Gln Ser
                 50                  55                  60

Phe Tyr Ser Thr Arg Pro Pro Ser Ile His Lys Asp Tyr Val Asn Arg
                 65                  70                  75

Leu Phe Leu Asn Trp Thr Glu Gly Gln Glu Ser Gly Phe Leu Arg Ile
                 80                  85                  90

Ser Asn Leu Arg Lys Glu Asp Gln Ser Val Tyr Phe Cys Arg Val Glu
                 95                 100                 105

Leu Asp Thr Arg Arg Ser Gly Arg Gln Gln Leu Gln Ser Ile Lys Gly
110                 115                 120                 125

Thr Lys Leu Thr Ile Thr Gln Ala Val Thr Thr Thr Thr Thr Trp Arg
                130                 135                 140

Pro Ser Ser Thr Thr Thr Ile Ala Gly Leu Arg Val Thr Glu Ser Lys
                145                 150                 155

Gly His Ser Glu Ser Trp His Leu Ser Leu Asp Thr Ala Ile Arg Val
                160                 165                 170

Ala Leu Ala Val Ala Val Leu Lys Thr Val Ile Leu Gly Leu Leu Cys
                175                 180                 185

Leu Leu Leu Leu Trp Trp Arg Arg Arg Lys Gly Ser Arg Ala Pro Ser
190                 195                 200                 205

Ser Asp Phe

<210> SEQ ID NO 5
<211> LENGTH: 1255
<212> TYPE: DNA
<213> ORGANISM: Homo sapiens
<220> FEATURE:
<221> NAME/KEY: sig_peptide
<222> LOCATION: (175)..(240)

<400> SEQUENCE: 5
ggaggccggg gcggggcggg cgcagccggc gctgagcttg cagggccgct ccccctcaccc      60 gcccccttcg agtccccggg cttcgcccca cccggcccgt gggggagtat ctgtcctgcc     120
gccttcgccc acgccctgca ctccgggacc gtccctgcgc gctctgggcg caccatggcc     180
cgcggggctg cgctggcgct gctgctcttc ggcctgctgg gtgttctggt cgccgcccg     240 gatggtggtt tcgatttatc cgatgccctt cctgacaatg aaaacaagaa acccactgca     300
atccccaaga aacccagtgc tggggatgac tttgacttag agatgctgt tgttgatgga     360
```

```
gaaaatgacg acccacgacc accgaaccca cccaaaccga tgccaaatcc aaaccccaac    420
caccctagtt cctccggtag cttttcagat gctgaccttg cggatggcgt ttcaggtgga    480
gaaggaaaag gaggcagtga tggtggaggc agccacagga agaaggggga agaggccgac    540
gccccaggcg tgatccccgg gattgtgggg gctgtcgtgg tcgccgtggc tggagccatc    600
tctagcttca ttgcttacca gaaaaagaag ctatgcttca agaaaatgc agaacaaggg     660 gaggtggaca tggagagcca ccggaatgcc aacgcagagc cagctgttca gcgtactctt    720
ttagagaaat agaagattgt cggcagaaac agcccaggcg ttggcagcag ggttagaaca    780
gctgcctgag gctcctccct gaaggacacc tgcctgagag cagagatgga ggccttctgt    840
tcacggcgga ttctttgttt taatcttgcg atgtgctttg cttgttgctg gcggatgat     900 gtttactaac gatgaatttt acatccaaag ggggataggc acttggaccc ccattctcca    960
aggcccgggg gggcggtttc ccatgggatg tgaaaggctg gccattatta agtccctgta   1020
actcaaatgt caaccccacc gaggcacccc ccgtcccccc agaatcttgg ctgtttacaa   1080
atcacgtgtc catcgagcac gtctgaaacc cctggtagcc ccgacttctt tttaattaaa   1140
ataaggtaag cccttcaatt tgtttcttca atatttcttt catttgtagg gatatttgtt   1200
tttcatatca gactaataaa aagaaattag aaaccaaaaa aaaaaaaaaa aaaaa        1255
```

<210> SEQ ID NO 6
<211> LENGTH: 185
<212> TYPE: PRT
<213> ORGANISM: Homo sapiens
<220> FEATURE:
<221> NAME/KEY: SIGNAL
<222> LOCATION: (1)..(22)
<220> FEATURE:
<221> NAME/KEY: mat_peptide
<222> LOCATION: (23)..(185)

<400> SEQUENCE: 6

```
Met Ala Arg Gly Ala Ala Leu Ala Leu Leu Phe Gly Leu Leu Gly
    -20              -15                 -10

Val Leu Val Ala Ala Pro Asp Gly Gly Phe Asp Leu Ser Asp Ala Leu
    -5               -1  1               5                   10

Pro Asp Asn Glu Asn Lys Lys Pro Thr Ala Ile Pro Lys Lys Pro Ser
                15                  20                  25

Ala Gly Asp Asp Phe Asp Leu Gly Asp Ala Val Val Asp Gly Glu Asn
                30                  35                  40

Asp Asp Pro Arg Pro Pro Asn Pro Pro Lys Pro Met Pro Asn Pro Asn
                45                  50                  55

Pro Asn His Pro Ser Ser Ser Gly Ser Phe Ser Asp Ala Asp Leu Ala
                60                  65                  70

Asp Gly Val Ser Gly Gly Glu Gly Lys Gly Ser Asp Gly Gly Gly
75                  80                  85                  90

Ser His Arg Lys Glu Gly Glu Glu Ala Asp Ala Pro Gly Val Ile Pro
                    95                  100                 105

Gly Ile Val Gly Ala Val Val Ala Val Ala Gly Ala Ile Ser Ser
                    110                 115                 120

Phe Ile Ala Tyr Gln Lys Lys Lys Leu Cys Phe Lys Glu Asn Ala Glu
                125                 130                 135

Gln Gly Glu Val Asp Met Glu Ser His Arg Asn Ala Asn Ala Glu Pro
                140                 145                 150

Ala Val Gln Arg Thr Leu Leu Glu Lys
155                 160
```

```
<210> SEQ ID NO 7
<211> LENGTH: 1207
<212> TYPE: DNA
<213> ORGANISM: Homo sapiens
<220> FEATURE:
<221> NAME/KEY: sig_peptide
<222> LOCATION: (175)..(240)

<400> SEQUENCE: 7
ggaggccggg gcggggcggg cgcagccggc gctgagcttg cagggccgct cccctcaccc    60 gccccttcg  agtccccggg cttcgcccca cccggcccgt gggggagtat ctgtcctgcc   120
gccttcgccc acgccctgca ctccgggacc gtccctgcgc gctctgggcg caccatggcc   180
cgcggggctg cgctggcgct gctgctcttc ggcctgctgg gtgttctggt cgccgccccg   240
gatggtggtt tcgatttatc cgatgccctt cctggggatg actttgactt aggagatgct   300
gttgttgatg gagaaaatga cgacccacga ccaccgaacc cacccaaacc gatgccaaat   360
ccaaacccca accaccctag ttcctccggt agcttttcag atgctgacct tgcggatggc   420
gtttcaggtg gagaaggaaa aggaggcagt gatggtggag gcagccacag gaaagaaggg   480
gaagaggccg acgccccagg cgtgatcccc gggattgtgg gggctgtcgt ggtcgccgtg   540
gctggagcca tctctagctt cattgcttac agaaaaaga agctatgctt caaagaaaat   600
gcagaacaag gggaggtgga catggagagc caccggaatg ccaacgcaga gccagctgtt   660
cagcgtactc ttttagagaa atagaagatt gtcggcagaa acagcccagg cgttggcagc   720
agggttagaa cagctgcctg aggctcctcc ctgaaggaca cctgcctgag agcagagatg   780
gaggccttct gttcacggcg gattctttgt tttaatcttg cgatgtgctt tgcttgttgc   840
tgggcggatg atgtttacta acgatgaatt ttacatccaa aggggatag gcacttggac    900 ccccattctc caaggcccgg gggggcggtt tccatgggag tgtgaaaggc tggccattat   960
taagtccctg taactcaaat gtcaaccccca ccgaggcacc cccccgtccc ccagaatctt  1020
ggctgtttac aaatcacgtg tccatcgagc acgtctgaaa ccctggtag ccccgacttc   1080 tttttaatta aaataaggta agcccttcaa tttgtttctt caatatttct ttcatttgta  1140
gggatatttg ttttcatat  cagactaata aaagaaatt agaaaccaaa aaaaaaaaaa  1200
aaaaaaa                                                            1207

<210> SEQ ID NO 8
<211> LENGTH: 169
<212> TYPE: PRT
<213> ORGANISM: Homo sapiens
<220> FEATURE:
<221> NAME/KEY: SIGNAL
<222> LOCATION: (1)..(22)
<220> FEATURE:
<221> NAME/KEY: mat_peptide
<222> LOCATION: (23)..(169)

<400> SEQUENCE: 8

Met Ala Arg Gly Ala Ala Leu Ala Leu Leu Leu Phe Gly Leu Leu Gly
            -20                 -15                 -10

Val Leu Val Ala Ala Pro Asp Gly Gly Phe Asp Leu Ser Asp Ala Leu
 -5                  -1  1               5                   10

Pro Gly Asp Asp Phe Asp Leu Gly Asp Ala Val Val Asp Gly Glu Asn
                15                  20                  25

Asp Asp Pro Arg Pro Pro Asn Pro Pro Lys Pro Met Pro Asn Pro Asn
            30                  35                  40
```

```
Pro Asn His Pro Ser Ser Ser Gly Ser Phe Ser Asp Ala Asp Leu Ala
        45              50              55

Asp Gly Val Ser Gly Gly Glu Gly Lys Gly Gly Ser Asp Gly Gly Gly
    60              65              70

Ser His Arg Lys Glu Gly Glu Glu Ala Asp Ala Pro Gly Val Ile Pro
75              80              85              90

Gly Ile Val Gly Ala Val Val Val Ala Val Ala Gly Ala Ile Ser Ser
                95              100             105

Phe Ile Ala Tyr Gln Lys Lys Lys Leu Cys Phe Lys Glu Asn Ala Glu
            110             115             120

Gln Gly Glu Val Asp Met Glu Ser His Arg Asn Ala Asn Ala Glu Pro
        125             130             135

Ala Val Gln Arg Thr Leu Leu Glu Lys
        140         145
```

METHODS OF TREATING MULTIPLE SCLEROSIS, RHEUMATOID ARTHRITIS AND INFLAMMATORY BOWEL DISEASE USING AGONISTS ANTIBODIES TO PILR-α

This filing is a 371 of PCT Patent Application No. PCT/US2010/059893, filed Dec. 10, 2010, which claims benefit from Provisional Patent Application 61/287,584, filed Dec. 17, 2009, each of which is incorporated herein by reference.

The Sequence Listing filed electronically herewith is also hereby incorporated by reference in its entirety (File Name: "BP2009.7095-US-PCT_SeqListing"; Date Created: Jun. 15, 2012; File Size: 18.4 KB.)

FIELD OF THE INVENTION

The present invention provides methods of treating immune disorders, such as allergic, autoimmune and chronic inflammatory disorders, through modulation of the immune system.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells (including helper T cells, Th cells), B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration.

Although the immune system has a beneficial role in protection from infections and malignancies, inappropriate and/or uncontrolled immune responses can lead to immunopathology. Immune response can produce pathological consequences, e.g., when it involves excessive inflammation, as in the autoimmune disorders. See, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350. Inappropriate immune responses include allergic responses to an innocuous environmental antigens, such an a Th2-biased immune response. Immunopathology can also result from cell-based immune responses that occur in the absence of infection, or persist after resolution of an initial triggering infection. Chronic inflammation can also result from inappropriate immune response to self-antigens, as in the case of autoimmune disease, or other persistent antigens (such as commensal flora). Autoimmune inflammatory disorders include inflammation of the joints, central nervous system (CNS), skin, gut and other organs. Such diseases include rheumatoid arthritis (RA), multiple sclerosis (MS), psoriasis (Pso), and inflammatory bowel disorder (IBD), including Crohn's disease (CD) and ulcerative colitis (UC).

RA is a progressive, systemic disease characterized by inflammation of the synovial joints affecting about 0.5% of the world's population. Emery (2006) BMJ 332:152-155. Joint inflammation can lead to deformity, pain, stiffness and swelling, and ultimately to irreversible deterioration of the joint. Affected joints include knees, elbows, neck and joints of the hands and feet. Conventional treatment involves use of NSAIDs to alleviate symptoms, followed by administration of disease modifying antirheumatic drugs (DMARDs) such as gold, penicillamine, sulfasalazine and methotrexate. Recent advances include treatment with TNF-α inhibitors, including monoclonal antibodies, such as infliximab (REMICADE®), adalimumab (HUMIRA®) and golimumab (SIMPONI®), and receptor fusion proteins, such as etanercept (ENBREL®), and other TNF-α antagonists such as certolizumab pegol (CIMZIA®), golimumab, and natalizumab (TYSABRI®). Treatment with these TNF-α inhibitors dramatically reduces structural damage from the disease.

MS is thought to be an autoimmune disease of the central nervous system (CNS) involving loss of myelin from nerve fibers, resulting in plaques or lesions. The most common form is relapsing/remitting MS in which well defined symptomatic flare-ups occur, followed by periods of partial or complete remission. Conventional treatment options include interferon-β-1a and -1b, mitoxantrone, the tetrapeptide glatiramer acetate, therapeutic alpha-4-integrin-specific antibodies (natalizumab), or small molecule antagonists of alpha-4-integrin (e.g. those disclosed at WO 2003/084984).

The skin serves as an important boundary between the internal milieu and the environment, preventing contact with potentially harmful antigens. In the case of antigen/pathogen penetration, an inflammatory response is induced to eliminate the antigen. This response leads to a dermal infiltrate that consists predominantly of T cells, polymorphonuclear cells, and macrophages (see, e.g., Williams and Kupper (1996) *Life Sci.*, 58:1485-1507.) Normally, this inflammatory response, triggered by the pathogen, is under tight control and will be halted upon elimination of the pathogen.

Psoriasis is characterized by T cell mediated hyperproliferation of keratinocytes coupled with an inflammatory infiltrate. The disease has certain distinct overlapping clinical phenotypes including chronic plaque lesions, skin eruptions, and pustular lesions (see, e.g., Gudjonsson et al. (2004) *Clin Exp. Immunol.* 135:1-8). Approximately 10% of psoriasis patients develop arthritis. The disease has a strong but complex genetic predisposition, with 60% concordance in monozygotic twins. The typical psoriatic lesion is a well defined erythematosus plaque covered by thick, silvery scales. The inflammation and hyperproliferation of psoriatic tissue is associated with a different histological, antigenic, and cytokine profile than normal skin. Among the cytokines associated with psoriasis are: TNFα, IL-19, IL-18, IL-15, IL-12, IL-7, IFNγ, IL-17A and IL-23 (see Gudjonsson et al., supra).

Crohn's disease and ulcerative colitis (collectively Inflammatory Bowel Disease, or IBD) are chronic, inflammatory diseases of the gastrointestinal tract. Both disorders are characterized by abdominal pain, diarrhea (often bloody), a variable group of "extra-intestinal" manifestations (such as arthritis, uveitis, skin changes, etc.) and the accumulation of inflammatory cells within the small intestine and colon. Additional symptoms, aspects, manifestations, or signs of IBD include malabsorption of food, altered bowel motility, infection, fever, rectal bleeding, weight loss, signs of malnutrition, perianal disease, abdominal mass, and growth failure, as well as intestinal complications such as stricture, fistulas, toxic megacolon, perforation, and cancer, and including endoscopic findings, such as, friability, aphthous and linear ulcers, cobblestone appearance, pseudopolyps, and rectal involvement and, in addition, anti-yeast antibodies. See, e.g., Podolsky (2002) *New Engl. J. Med.* 347:417-429; Hanauer (1996) *New Engl. J. Med.* 334:841-848; Horwitz and Fisher (2001) *New Engl. J. Med.* 344:1846-1850.

IBD affects both children and adults, and has a bimodal age distribution (one peak around 20, and a second around 40). IBD affects over 600,000 Americans. IBD is a chronic, lifelong disease, and is often grouped with "autoimmune" disorders (e.g. rheumatoid arthritis, type I diabetes mellitus, multiple sclerosis, etc.). IBD is found almost exclusively in the industrialized world. An estimated one million Americans are believed to have IBD, half of which have CD and half of which have UC. Hanauer (2006) *Inflamm. Bowel Dis.* 12:S3. There is an unexplained trend towards increasing incidence of IBD, particularly Crohn's Disease, in the U.S. and Europe.

Treatment of IBD is varied. First line therapy typically includes salicylate derivatives (e.g. 5-ASA) given orally or rectally. Corticosteroids (e.g. prednisone) are also used, despite the untoward side-effects, as well as immunomodulators such as sulfasalazine, azathioprine, methotrexate and 6-mercaptopurine, or an antibiotic (e.g. metronidazole) for Crohn's disease. Therapeutic monoclonal antibody treatments include infliximab (REMICADE®), a chimeric antibody directed to TNF-$\alpha$, and other TNF-$\alpha$ antagonists such as adalimumab ( HUMIRA®), certolizumab pegol (CIMZIA®), golimumab, and natalizumab ( TYSABRI®).

The need exists for therapeutic agents and methods for treatment of immune disorders, such as allergic responses, autoimmune and inflammatory disorders, such as those that occur in the CNS, skin, joints and gut.

SUMMARY OF THE INVENTION

The present invention addresses the need for improved therapeutic agents and methods for treatment of immune disorders, such as autoimmune and inflammatory disorders, by inhibition of paired-immunoglobulin type 2-like receptor $\beta$ (PILR$\beta$) or activation of paired-immunoglobulin type 2-like receptor $\Delta$ (PILR$\alpha$).

Accordingly, the present invention provides methods of treatment of a number of immune disorders, such as multiple sclerosis (MS), inflammatory bowel disease (IBD), rheumatoid arthritis (RA), psoriasis (Pso), allograft rejection, autoimmune thyroid disease, autoimmune uveitis, scleritis, autoimmune glomerulonephritis, giant cell arteritis, insulin-dependent diabetes mellitus (IDDM), pernicious anemia, psoriasis, sarcoidosis, scleroderma, graft versus host disease (GVHD) and systemic lupus erythematosus (SLE). In selected embodiments the immune disorder is MS, RA or IBD. The present invention also provides methods of treatment of allergic disorders, such as airway hypersensitivity, and methods of immunotherapy (e.g. inducing tolerance by use of sublingual allergy vaccines).

The present invention provides a method of treating an immune disorder comprising administering to a subject in need of such treatment, an effective amount of an antagonist of PILR$\beta$. In certain embodiments, antagonist of PILR$\beta$ is an antibody, antibody fragment, or antibody conjugate, including a polyclonal antibody, a monoclonal antibody, a recombinant antibody, a humanized antibody or fragment thereof, a fully human antibody or fragment thereof. The antagonist can also be a soluble polypeptide fragment of PILR$\beta$, or a soluble PILR$\beta$ polypeptide fused to a heterologous protein. For example, a soluble PILR$\beta$ polypeptide or fusion polypeptide may comprise residues 20-191 of SEQ ID NO: 4. The invention also provides that the antagonist of PILR$\beta$ is administered with at least one other therapeutic agent, such as an immunosuppressant.

In other embodiments the antagonist of PILR$\beta$ comprises a polynucleotide. In various embodiments the polynucleotide is an antisense nucleic acid (e.g. antisense RNA) or an interfering nucleic acid, such as a small interfering RNA (siRNA). In one embodiment the polynucleotide antagonist of PILR$\beta$ is delivered in gene therapy vector, such as an adenovirus, lentivirus, retrovirus or adenoassociated virus vector. In another embodiment the polynucleotide antagonist of PILR$\beta$ is delivered as a therapeutic agent.

The present invention encompasses a method of treating an immune disorder comprising administering to a subject in need of such treatment, an effective amount of an agonist of PILR$\alpha$. In one embodiment, the agonist of PILR$\alpha$ is an antibody, antibody fragment, or antibody conjugate, including a polyclonal antibody, a monoclonal antibody, a recombinant antibody, a humanized antibody or fragment thereof, a fully human antibody or fragment thereof. The invention also provides that the agonist of PILR$\alpha$ is administered with at least one other therapeutic agent, such as an immunosuppressant.

In still further embodiments, the agonist of PILR$\alpha$ is ligand, such as CD99, or a CD99-like molecule, or a PILR-binding fragment thereof. In some embodiments, the agonist of PILR$\alpha$ is a polynucleotide encoding CD99, or a PILR-binding fragment thereof, optionally in a vector for delivery and expression of the CD99 gene.

BRIEF DESCRIPTION OF THE DRAWINGS

FIG. 4A shows survival of PILR$\beta$-/- and wildtype (WT) mice in a mouse model of inflammatory bowel disease (IBD) involving per-oral infection with high dose *Toxoplasma gondii* at various timepoints after infection. FIGS. 4B and 4C show PILR$\beta$ and PILR$\alpha$ mRNA expression (in normalized units), respectively, in the ileum of these same PILR$\beta$-/- and WT mice at various timepoints after infection. See Example 7.

(FIGS. 5B and 5D) after peroral infection. Results are shown for one representative experiment, n=5/group. *p<0.04; **p<0.004. Specifically, for IFNγ, day 7 STAg, p=0.0395; day 7 αCD3, p=0.0243. For IL-10, day 7 αCD3, p=0.0358; day 10 STAg, p=0.0348; day 10 αCD3, p=0.0039. See Example 7.

FIG. 8A shows PILRα and PILRβ mRNA expression (in normalized units) determined by RT-PCR in brain mononuclear cells (BMNCs) isolated from the CNS of WT or PILRβ–/– encephalitis mice 60-90 days post-infection. One representative experiment is shown. FIGS. 8B and 8C show serum protein levels of IL-27p28, as determined by ELISA, in samples from either acutely (day 5, FIG. 8B) or chronically (day 60, FIG. 8C) infected encephalitis mice. PBS in FIG. 8B refers to phosphate buffered saline control mice, and INF refers to mice dosed with *T. gondii* to induce encephalitis. Serum IL-27p28 was significantly higher in PILRβ–/– (triangles) than in WT (circles) mice at both time points, with day 5 p=0.0007 and day 60 p=0.0104. Pooled data from two experiments are shown in FIG. 8C, n=5-6/group. FIG. 8D shows survival of PILRβ–/– and WT encephalitis mice. See Example 8.

FIGS. 10A-10E show mRNA expression for PILRα, IL-10, TNFα, IL-6 and MIP2, respectively. See Example 9.

DETAILED DESCRIPTION

As used herein, including the appended claims, the singular forms of words such as "a," "an," and "the," include their corresponding plural references unless the context clearly dictates otherwise.

All references cited herein are incorporated by reference to the same extent as if each individual publication, patent application, or patent, was specifically and individually indicated to be incorporated by reference.

Unless otherwise indicated or clear from the context, gene/protein names (e.g. PILR, CD99, cytokines, etc.) refer to the protein rather than the gene. Unless otherwise indicated, gene/protein names referenced in the context of experiments with mice refer to the mouse forms of the proteins or genes, whereas gene/protein names referenced in the context of human therapeutics refer to the human forms.

I. Definitions

The terms "PILRα or PILRβ", "Paired-immunoglobulin type 2-like receptor α or β", "FDF03 inhibitory receptor and FDF03 activating receptor" are well known in the art. "PILR" and "PILRα/β" represent "PILRα and PILRβ" unless otherwise specified.

"Antagonists of PILRβ activity" or "PILRβ antagonists" as used herein, refers to agents that block or at least reduce the activating activity of PILRβ. Such antagonists include antagonist antibodies or antigen binding fragments thereof, soluble fragments of PILRβ (e.g. residues 20-191 of SEQ ID NO: 4), PILRβ fusion proteins, etc., that can inhibit the biological results of PILRβ activation. Fusion proteins are usually the soluble domain polypeptide of PILRβ associated with a heterologous protein or synthetic molecule, e.g., the Ig domain of an immunoglobulin. Antagonists also include nucleic acid antagonists, such as interfering nucleic acids (e.g. siRNA) and antisense nucleic acids, whether delivered polynucleotides as drugs per se, or as incorporated in vectors, such as gene therapy vectors, to facilitate their delivery and expression. An agent may be considered an antagonist of PILRβ, for example, if it specifically binds to PILRβ and either significantly reduces antigen-specific proliferation of lymph node T cells obtained from in EAE mice, reduces expression of MIP2 in macrophages (Example 9 and FIGS. 10E and 10F), or blocks mast cell degranulation under conditions where such degranulation of mast cells would otherwise be induced through PILRβ, e.g. by CD99 (SEQ ID NOs: 6 and 8) or a mature form thereof (Example 2), as described in greater detail herein.

Figure 2A:
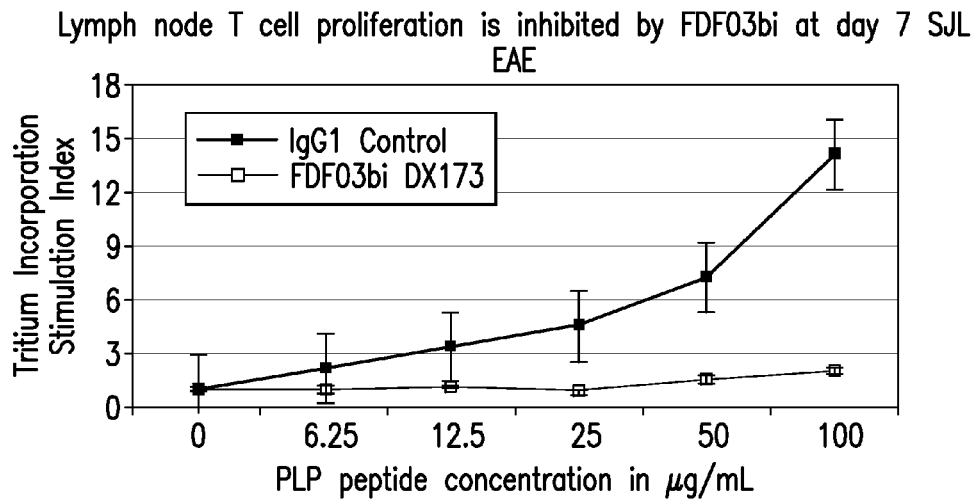
FIG. 2A shows T cell proliferation (as measured by incorporation of tritium labeled thymidine) for lymph node cells cultured in the presence of DX173) or in the presence of an IgG1 isotype control, in the presence or absence of varying concentrations of immunizing peptide (PLP). Tritium incorporation is reported as a "Stimulation Index," which is the ratio of tritium incorporation in a given culture to tritium incorporation in a culture without PLP. See Example 5.
Figure 2B:
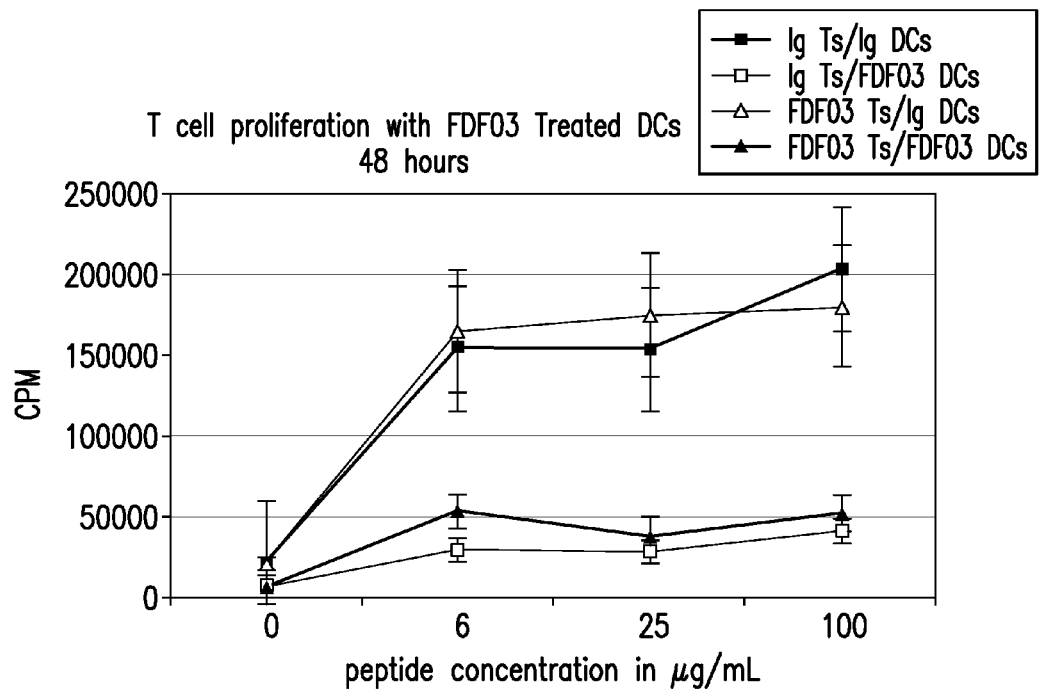
FIG. 2B shows T cell proliferation (measured by incorporation of tritium labeled thymidine) for lymph node cells cultured in the presence of DX173 or in the presence of an IgG1 isotype control, in the presence or absence of varying concentrations of immunizing peptide (PLP). Tritium incorporation is reported as raw counts per minute (CPM). See Example 5.
Figure 3A:
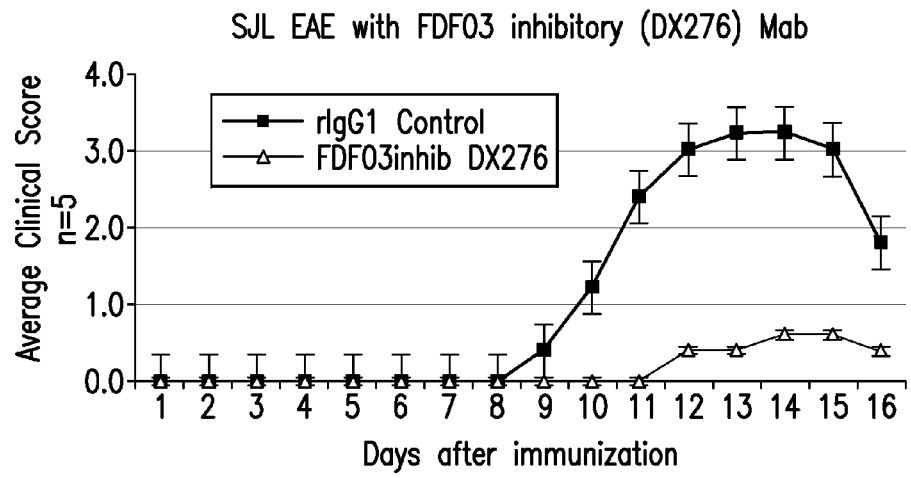
FIG. 3A presents average clinical scores in EAE mice treated with agonist antibodies to FDF03inhib (the inhibitory form of FDF03, aka PILR$\alpha$) or isotype control.

"Agonists of PILRα activity" or "PILRα agonists" as used herein, refers to agents that enhance the inhibitory activity of PILRα. Such agonists include agonist antibodies or antigen binding fragments thereof, natural ligands such as human CD99 or a CD99-like molecule, or a PILR-binding fragment of such CD99 or CD99-like molecule, etc., that can mimic the biological results of PILRα activation. CD99-like molecule, as used herein, refers to any human ortholog of the mouse PILR ligand disclosed at Shiratori et al. (2004) *J. Exp. Med.* 199:525-533. The sequences for two isoforms of one such molecule are provided at SEQ ID NOs: 5-8. Agonists also include nucleic acids encoding any of these protein agonists, including nucleic acids incorporated in vectors, such as gene therapy vectors, to facilitate their delivery and expression. An agent may be considered an agonist of PILRα, for example, if it specifically binds to PILRα and either significantly reduces antigen-specific proliferation of lymph node T cells obtained from EAE mice (Example 5 and FIG. 2), reduces expression of MIP2 in macrophages, or blocks mast cell degranulation under conditions where such degranulation of mast cells would otherwise be induced through PILRβ, e.g. by CD99 (SEQ ID NOs: 6 and 8) or a mature form thereof, or by an agonist antibody for PILRβ, as described in greater detail herein. See Example 2. Although it may be preferred that the PILRα agonist of the present invention not significantly bind to (cross-react with) PILRβ, some agents may also be effective as PILRα agonists of the present invention despite cross-reacting with PILRβ. See, e.g., FIGS. 1, 3A and 3B.

To examine the extent of modulation of PILR activity, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts PILR, e.g., in the fluid phase or colloidal phase, but also situations where the agonist or antagonist does not contact the cell or the receptor. As used herein, "inhibit" or "treat" or "treatment" includes a postponement of development of the symptoms associated with a microbial infection and/or a reduction in the severity of such symptoms that will or are expected to develop. Thus, the terms denote that a beneficial result has been conferred on a vertebrate subject with an microbial infection, or with the potential to develop such a disease or symptom.

Unless otherwise indicated, "immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects. See, e.g., U.S. Pat. No. 5,888, 530. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

"Binding" refers to an association of the binding composition with a target where the association results in reduction in the normal Brownian motion of the binding composition, in cases where the binding composition can be dissolved or suspended in solution.

As used herein, the term "antibody" refers to any form of antibody that exhibits the desired biological activity. Thus, it is used in the broadest sense and specifically covers polyclonal antibodies, monoclonal antibodies (including full length monoclonal antibodies), multispecific antibodies (e.g. bispecific antibodies), chimeric antibodies, humanized antibodies, fully human antibodies, etc., so long as they exhibit the desired biological activity.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) J. Mol. Biol. 196: 901-917). As used herein, the term "framework" or "FR" residues refers to those variable domain residues other than the hypervariable region residues defined herein as CDR residues.

As used herein, the terms "PILR binding fragment," "binding fragment thereof" or "antigen binding fragment thereof" encompass a fragment or a derivative of an antibody that still substantially retains its biological activity of either stimulating PILRα activity or inhibiting PILRβ activity, such inhibition being referred to herein as "PILR modulating activity." The term "antibody fragment" or "PILR binding fragment" refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its PILR modulatory activity. Preferably, a binding fragment or derivative retains at least 25%, 50%, 60%, 70%, 80%, 90%, 95%, 99% or 100% (or more) of its PILR activity, although any binding fragment with sufficient affinity to exert the desired biological effect will be useful. It is also intended that a PILR binding fragment can include variants having conservative amino acid substitutions that do not substantially alter its biologic activity.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) Proc. Natl. Acad. Sci. USA 81: 6851-6855. For example, a chimeric antibody for use as a human therapeutic may comprise rodent variable domains coupled with human constant regions.

As used herein, the term "humanized antibody" refers to forms of antibodies that contain variable domain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of a human immunoglobulin constant region (Fc). The humanized forms of rodent antibodies will generally comprise the same CDR sequences of the parental rodent antibodies, although certain amino acid substitutions may be included to increase affinity, increase stability of the humanized antibody, or for other reasons.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may bind the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994)

THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

The antibodies of the present invention also include antibodies with modified (or blocked) Fc regions to provide altered effector functions. See, e.g., U.S. Pat. No. 5,624,821; WO 2003/086310; WO 2005/120571; WO 2006/0057702; Presta (2006) Adv. Drug Delivery Rev. 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) J. Allergy Clin. Immunol. 116:731 at 734-35.

The antibodies of the present invention also include antibodies with intact Fc regions that provide full effector functions, e.g. antibodies of human isotype IgG1, which induce complement-dependent cytotoxicity (CDC) or antibody dependent cellular cytotoxicity (ADCC) in the a targeted cell.

The antibodies of the present invention also include antibodies conjugated to cytotoxic payloads, such as cytotoxic agents or radionuclides. Such antibody conjugates may be used in immunotherapy to selectively target and kill cells expressing PILR on their surface. Exemplary cytotoxic agents include ricin, vinca alkaloid, methotrexate, Psuedomonas exotoxin, saporin, diphtheria toxin, cisplatin, doxorubicin, abrin toxin, gelonin and pokeweed antiviral protein. Exemplary radionuclides for use in immunotherapy with the antibodies of the present invention include $^{125}$I, $^{131}$I, $^{90}$Y, $^{67}$Cu, $^{211}$At, $^{177}$Lu, $^{143}$Pr and $^{213}$Bi. See, e.g., U.S. Patent Application Publication No. 2006/0014225.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. When used with reference to antibodies, the term "binding compound" refers to both antibodies and antigen binding fragments thereof. "Binding composition" refers to a molecule, e.g. a binding compound, in combination with a stabilizer, excipient, salt, buffer, solvent, or additive, capable of binding to a target.

The antibody, or binding compound derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) Analyt. Biochem. 107:220-239.

"Nucleic acid antagonists," as used herein, include antisense nucleic acids and "interfering nucleic acids," including siRNA and mechanistically related agents such as siNA and shRNA. Such agents may be directly administered as polynucleotide drugs per se, or may be incorporated into vectors to facilitate delivery.

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case PILR) if it binds to polypeptides comprising the sequence of PILR but does not bind to proteins lacking the sequence of PILR. For example, an antibody that specifically binds to a polypeptide comprising PILR may bind to a FLAG®-tagged form of PILR but will not bind to other FLAG®-tagged proteins.

With reference to proteins, "conservatively modified variants" or "conservative substitution" refers to substitutions of amino acids are known to those of skill in the art and may often be made even in essential regions of the polypeptide without altering the biological activity of the resulting molecule. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Those of skill in this art recognize that, in general, single amino acid substitutions, particularly in non-essential regions of a polypeptide, may not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences involved in the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid. RT-PCR refers to real time quantitative PCR of mRNA using reverse transcriptase, for example as a method of measuring gene expression. See Example 1.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset et al. (2003) *Biochem. Biophys. Res. Commun.* 307:198-205; Muyldermans (2001) *J. Biotechnol.* 74:277-302; L1 (2000) *Nat. Biotechnol.* 18:1251-1256; Apostolopoulos et al. (2002) *Curr. Med. Chem.* 9:411-420; Monfardini et al. (2002) *Curr. Pharm. Des.* 8:2185-2199; Domingues et al. (1999) *Nat. Struct. Biol.* 6:652-656; Sato and Sone (2003) *Biochem. J.* 371:603-608; U.S. Pat. No. 6,326,482.

"EAE mice" refers to mice treated with complete Freund's adjuvant (CFA) and pertussis toxin to induce CNS inflammation, as described at Examples 4, 5 and 6. "CAIA mice" refers to mice treated i.v. with Chemicon's arthrogen CIA cocktail to induce CAIA, as described at Examples 4 and 6. "IBD mice" refers to mice treated with per-oral *T. gondii* cysts to induce gut inflammation, as described at Examples 4 and 7. "Encephalitis mice" refers to mice treated (i.p.) with *T. gondii* cysts to induce CNS inflammation, as described at Examples 4 and 8.

II. Summary

Paired immunoglobulin-like receptor beta, PILRβ, is a DAP12 binding partner expressed on both human and mouse myeloid cells. PILRα is the inhibitory form of the receptors. The potential ligand for PILRα/β, CD99, is found on many cell types, such as epithelial cells, where it plays a role in migration of immune cells to sites of inflammation. An agonist antibody to PILRα was administered to mice that had been treated with CFA and pertussis toxin to produce CNS and joint inflammation as models of MS and RA. The agonist antibody to PILRα significantly reduced the severity of disease in both mouse models.

In addition, PILRβ deficient mice were challenged with high dose *Toxoplasma gondii* as a model of inflammatory bowel disease to understand the potential role of this receptor in inflammatory responses. Both macrophages and DCs from PILRβ deficient mice produced more IL-27p28 and promoted IL-10 production in effector T cells a compared with WT mice. The sustained production of IL-27 led ultimately to enhanced survival after challenge due to dampened immune pathology in the gut. Similar protection was also observed in the CNS during chronic *T. gondii* infection after i.p challenge.

These results suggest that PILRα and PILRβ are important for regulating aberrant inflammatory responses, and that PILRα agonists and PILRβ antagonist will be useful in treating immune disorders, such as autoimmune inflammatory diseases.

III. PILRα and PILRβ

Information relating to PILRα and PILRβ generally is helpful in understanding the present invention. As used herein, "PILR" refers to PILRα and PILRβ collectively, or individually, as the context dictates, and similarly "FDF03" refers to one or both of the inhibiting (PILRα) or activating (PILRβ) forms. The human and mouse PILRα and PILRβ nucleotide and polypeptide sequences are disclosed in WO 98/024906 and WO 00/040721, respectively. The nucleic acid and polypeptide sequences for human PILRα are also available at NM_013439.2 and NP_038467.2, which are provided at SEQ ID NOs: 1 and 2, respectively. PILRα is further described at Gene ID No. 29992. The nucleic acid and polypeptide sequences for human PILRβ are available at NM_013440.3 and NP_038468.3, which are provided at SEQ ID NOs: 3 and 4, respectively. PILRβ is further described at Gene ID No. 29990.

A potential ligand for PILR (both forms) is CD99. The nucleic acid and polypeptide sequences for human CD99 (long isoform) are available at NM_002414.3 and NP_002405.1, and are provided at SEQ ID NOs: 5 and 6, respectively. The nucleic acid and polypeptide sequences for human CD99 (short isoform) are available at NM_001122898.1 and NP_001116370.1, and are provided at SEQ ID NOs: 7 and 8, respectively. CD99 is further described at Gene ID No. 4267.

Dap12 is a modulator of the amplitude of an immune response, but in a very cell specific way (1). There are many receptors that pair with Dap12 whose expression patterns, in part help govern the ultimate consequence of Dap12 signaling. One receptor partner of Dap12 is the paired-immunoglobulin-like receptor-beta (PILRβ). PILRβ, known to be a type I glycoprotein with a single extracellular Ig-like domain and a truncated cytoplasmic tail (2). PILRβ does not contain its own activation motif, but is dependent on Dap12 for ITAM mediated signals. PILRα is the inhibitory form of the receptor containing an ITIM within its intracellular domain that is thought to bind SHP-1/2 upon phosphorylation (3) (2). PILRα and PILRβ are mainly expressed on cells of the myeloid lineage on both human and mouse populations, with most cells displaying both isoforms of this receptor on their surface. However, there is some differential expression between the paired receptors, with PILRβ as the primary isoform displayed by NK cells (4).

While expression of this paired receptor is relatively restricted, its potential ligands have a considerably more ubiquitous expression pattern. In mice, a CD99-like molecule was first identified on T cells as interacting with PILRβ on NK cells and activating their cytotoxic capacity (4). The same group also found that the CD99-like molecule was able to activate bone-marrow derived DCs and promote TNFα production. The ability of CD99 to bind PILRα and PILRβ was characterized as involving recognition of two O-glycosylated sites on CD99 and these sites are thought to be essential for stable interaction between receptor and ligand (5, 6). Despite the efficiency with which the activating receptor is triggered by CD99 and CD99-like molecules, it was discovered that the affinity of PILRα for CD99 binding is significantly higher than the affinity of PILRβ (5).

CD99 is a glycoprotein that is thought to modulate a number of immune responses related to inflammation. It is expressed on the surface of a large variety of immune cells and tissues including activated T cells (7). It may also play a role in regulating the migration of cells into tissues as it is also found on endothelial tight junctions where it has been shown to mediate immune cell extravasation from the blood (8-10). Additionally, the inhibitory receptor is also thought to act as a co-receptor for viral glycoprotein B allowing pathogen entry into the host cell and in some cases viral persistence (11, 12). There is an ever growing body of evidence to suggest that the CD99:PILRα/β interactions have a significant affect on the quality of the innate immune response.

Many DAP12 associated receptors have been shown to play key roles in regulating immune responses of macrophages and dendritic cells (DC) during inflammatory responses. We therefore, generated activating receptor-deficient mice to study the relevance of PILRβ in immune function. To specifically address the question of whether these receptors modulated the function of antigen presenting cells (APCs) found in the mucosal tissue, we employed a murine model of inflammatory bowel disease (IBD) to test the impact of abrogating the function of PILRβ. High dose peroral infection with the protozoan parasite, *Toxoplasma gondii* (*T. gondii*), promotes a robust Th1-type response that precipitates an aggressive immune-mediated pathology, causing necrosis of ileal villi, and resulting in the ultimate demise of the host within 7-14 days after challenge (13). This model of infection mimics other IBD models with regard to immunological mechanisms and histological changes. For example, it is known that CD4+ T cells play a critical role in mediating pathology after high-dose infection with *T. gondii*, and an aberrant response to commensal flora worsens outcome. Thus, the innate immune response greatly affects outcome and severity of disease by establishing and then continuing to promote inflammation well beyond the initiating injury.

IV. Treatment of Immune Disorders using Antagonists of PILRβ or Agonists of PILRα

The present invention provides methods of treatment of immune disorders using antagonists of PILRβ or agonists of PILRα. The present invention is based, at least in part, on the discovery that inhibition of PILRβ, or activation of PILRα, results in increased expression of interleukin 27 (IL-27). Without intending to be limited by theory, it is likely that the anti-inflammatory effects of IL-27 would be beneficial in reducing immunopathology in a number of autoimmune and inflammatory disorders. IL-27 enhances production of IL-10, which may be the proximate cause of the anti-inflammatory phenotype in PILRβKO mice. Regardless of the mechanism of action, it is observed that inhibition of PILRβ, or activation of PILRα, results in decreased immunopathology in two separate animal models of multiple sclerosis and in an animal model of rheumatoid arthritis, as illustrated by the examples and figures herein.

One advantage of the therapeutic agents and methods of the present invention is that they are based on promotion of an active anti-inflammatory response, rather than reduction of an immunopathological response. Accordingly, the methods presented herein would be expected to reduce immunopathology in any number of disorders regardless of etiology. Specifically, the agents and methods of the present invention would be expected to find us in treatment of any disorder in which agonism of IL-27 would be beneficial, which disorders might include Th1, Th2 or Th17 (and potentially other) disorders. For example, see Diveu et al. (2008) *Curr. Op. Immunol.* 20:663 for a discussion of the IL-27's anti-inflammatory role in suppressing immunopathology in Th17 and Th1 mediated inflammatory disorders.

Specifically, the results presented herein demonstrate that inhibition of PILRβ (or activation of PILRα) result in increased survival, and reduced pathology, in animal models of several human autoimmune inflammatory diseases. The results presented herein also demonstrate that inhibition of PILRβ (or activation of PILRα) results in increased production of IL-27. IL-27 has been shown to induce expression of IL-10, and is believed to limit overt activation of T cells irrespective of their lineage, e.g. Th1, Th17 and Th2. Goriely et al. (2009) *Allergy* 64:702. Accordingly, without intending to be limited by theory, inhibition of PILRβ (or activation of PILRα) would be expected to have beneficial effects in treatment of human disorders involving excessive Th1, Th17 and Th2 responses. For example, IL-27 has been associated with uveitis and scleritis (Amadi-Obi et al. (2007) *Nat. Med.* 13:711), autoimmune glomerulonephritis in lupus-prone mice (Sugyama et al. (2008) *Ann. Rheum. Dis.* 67:1461), and airway hypersensitivity (Stock et al. (2004) *Nat. Immunol.* 5:1149). Administration of agonists of TCCR (also known as IL-27R and WSX-1) has also been proposed for the treatment of a number of immune disorders, such as multiple sclerosis, inflammatory bowel disease, rheumatoid arthritis, allograft rejection, autoimmune thyroid disease, autoimmune uveoretinitis, autoimmune glomerulonephritis, giant cell arteritis, insulin-dependent diabetes mellitus, pernicious anemia, psoriasis, sarcoidosis, scleroderma, and systemic lupus erythematosus. U.S. Pat. App. No. 2006/0177436. IL-27 may also find use in inducing tolerance using sublingual allergy vaccines. Mascarell et al. (2008) *J. Allergy Clin. Immunol.* 122: 603; Cosmi et al. (2006) *Clin. Exp. Allergy* 36:261. The present invention also provides methods of treating graft versus host disease using antagonists of PILRβ or agonists of PILRα. See also WO 2008/025031, disclosing the opposite of the present invention, i.e. use of IL-27 antagonists, rather than agonists as disclosed herein, for the treatment of GVHD.

V. Experimental Results

Experimental results provided herein support the use of agonists of PILRα or antagonists of PILRβ to treat immune disorders.

Figure 3B:
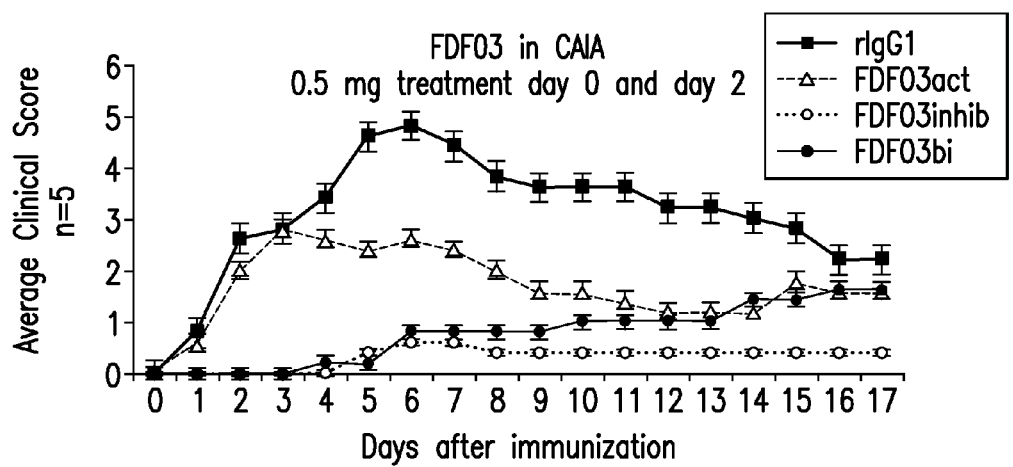
FIG. 3B presents average clinical scores in CAIA mice treated with agonist antibodies to FDF03act (the activating form of FDF03, aka PILR$\beta$), FDF03inhib (the inhibitory form of FDF03, aka PILR$\alpha$), bispecific antibody DX173, or isotype control. The antibody to FDF03inhib is referred to as DX276 and the antibody to FDF03act is referred to as DX266. See Example 6.

A first set of experiments was performed using agonist antibodies against PILRα and/or PILRβ to assess the roles of these receptors in immune pathology in animal models of IBD and MS. Mice were treated with CFA and pertussis toxin to induce CNS inflammation in a mouse EAE model of MS, or with a cocktail of collagen-specific antibodies to induce joint inflammation in a mouse CAIA model of IBD. EAE mice treated with a bispecific antibody to PILRα and PILRβ showed significantly reduced pathology (FIG. 1), perhaps as a result of reduced capacity of dendritic cells to stimulate T cell proliferation (FIG. 2). Experiments with separate antibodies specific for PILRα or PILRβ indicated that activation of PILRα (the inhibitory form of FDF03) with an agonist antibody was effective in reducing pathology in mouse models of multiple sclerosis (FIG. 3A) and rheumatoid arthritis (FIG. 3B). These results, taken as a whole, suggest that PILRα agonists may find use in treating MS, RA, and perhaps other related human diseases.

Figure 4A:
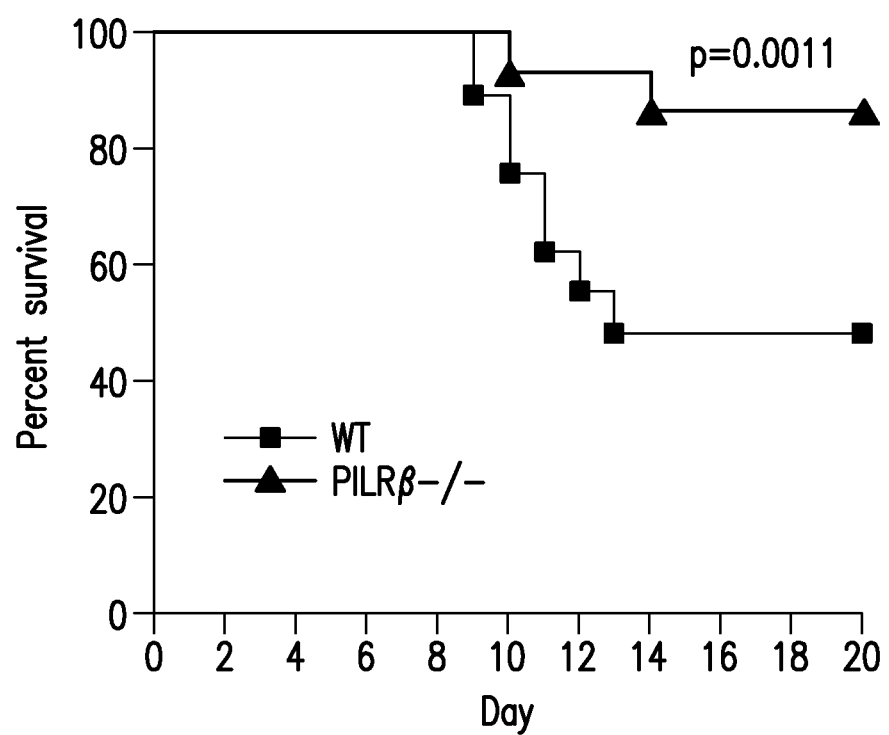
FIGS. 4A-4C show results obtained with FDF03act/PILR$\beta$ knockout (KO) mice (PILR$\beta$-/- mice).
Figure 4B:
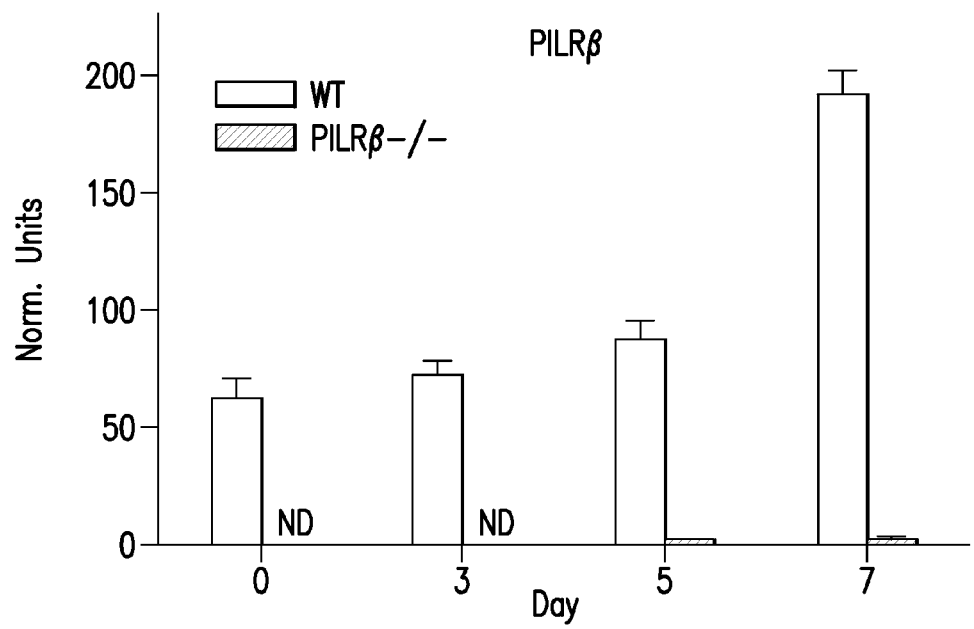
Figure 4C:
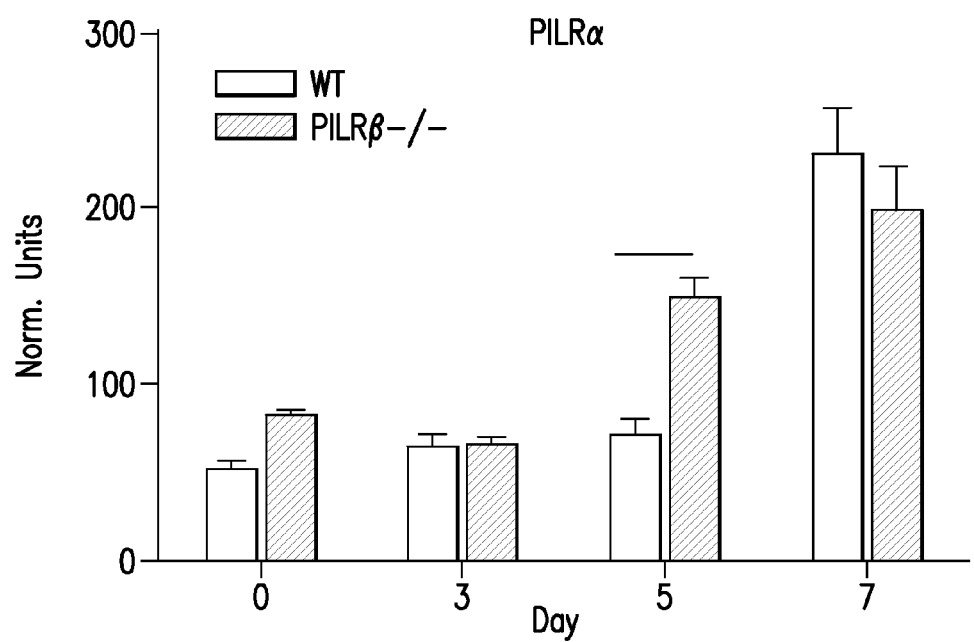

Additional experiments were performed using PILRβ–/– mice to assess the effects of PILRβ deficiency on immune response. A first experiment was performed to assess the ability of PILRβ–/– mice to survive in a mouse model of gut inflammation. As shown in FIG. 4A, while WT mice exhibited over 50% mortality by day 14, PILRβ–/– mice had significantly enhanced survival, with only 13% mortality. FIGS. 4B and 4C show that expression of both the activating (PILRβ) and inhibitory (PILRα) receptors increased in the ileum by day 7 in the WT IBD mice. However, a significantly greater increase in PILRα expression was observed in ileum from PILRβ–/– mice by day 5, suggesting that there is an earlier upregulation of the inhibitory receptor in the absence of its activating partner (FIG. 4C).

Figure 5A:
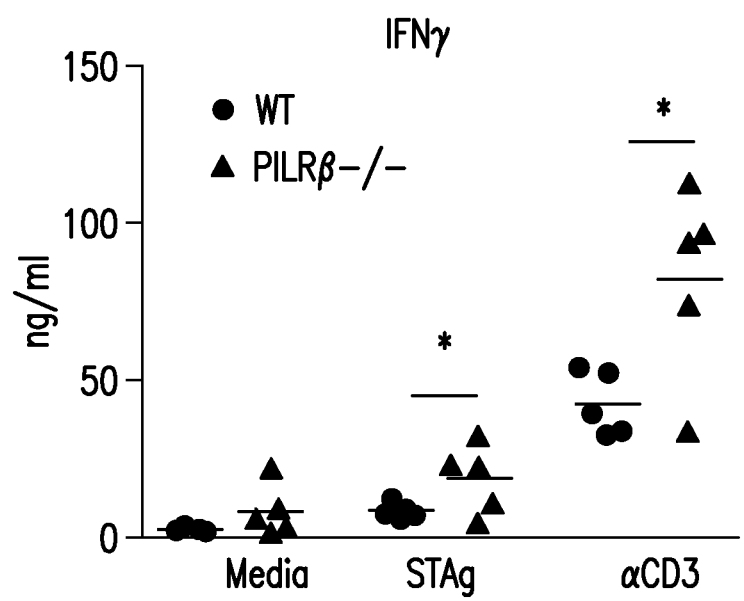
FIGS. 5A-5D show IFN$\gamma$ and IL-10 detectable in supernatants of splenocyte cultures after 3 days of culture in media alone, with STAg or with $\alpha$CD3. Results are presented for splenocytes obtained at day 7 (FIGS. 5A and 5C) or day 10

Further experiments demonstrated that enhanced resistance of PILRβ–/– mice to lethal infection was associated with increases in both IFNγ and IL-10 production by T cells. Locally, inflammation can be regulated by cellular recruitment to the tissue and the resultant milieu of cytokines To determine whether PILR signaling can indeed affect either of these aspects of the immune response, histological analysis of ileum from both WT and PILRβ–/– mice after infection was performed. Overall, WT sections of ileum revealed the presence of more cellular infiltrate in the mucosa and more blood compared to KO sections 10 days after challenge (images not shown). Additionally, spleens were harvested and cultured in recall assays at 7 and 10 days post-infection, respectively, and supernatants were analyzed for the presence of cytokine Results show significantly more IFNγ production in response to soluble *Toxoplasma* antigen (STAg) or αCD3 restimulation at day 7 (FIG. 5A). Interestingly, by day 10, splenocyte cultures exhibited no difference in IFNγ production between strains (FIG. 5B), supporting a more tissue specific role for FDF03/PILR.

Figure 5B:
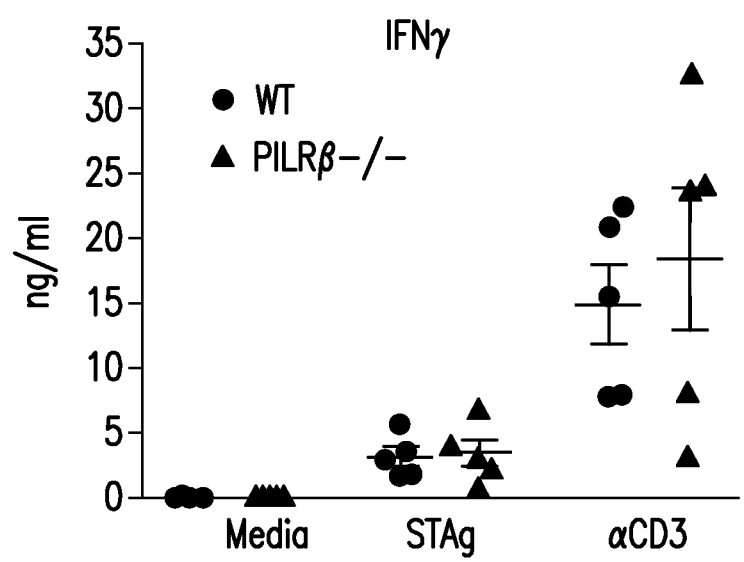
Figure 5C:
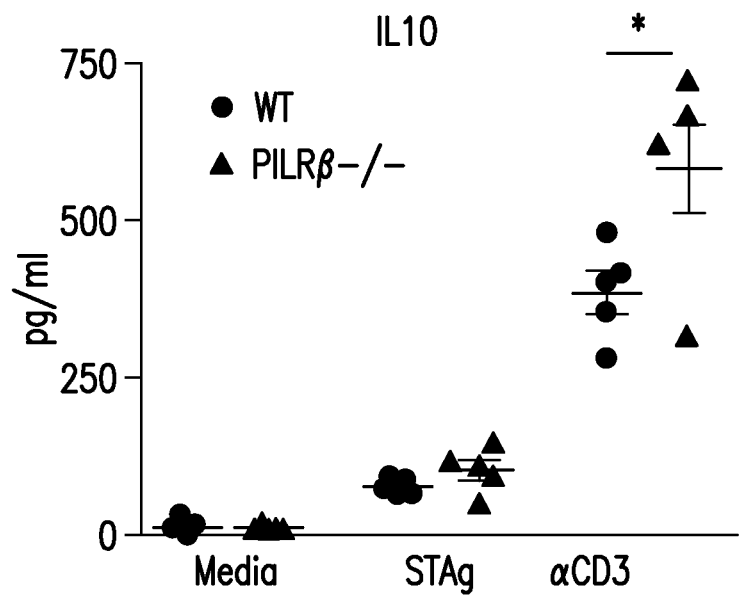
Figure 5D:
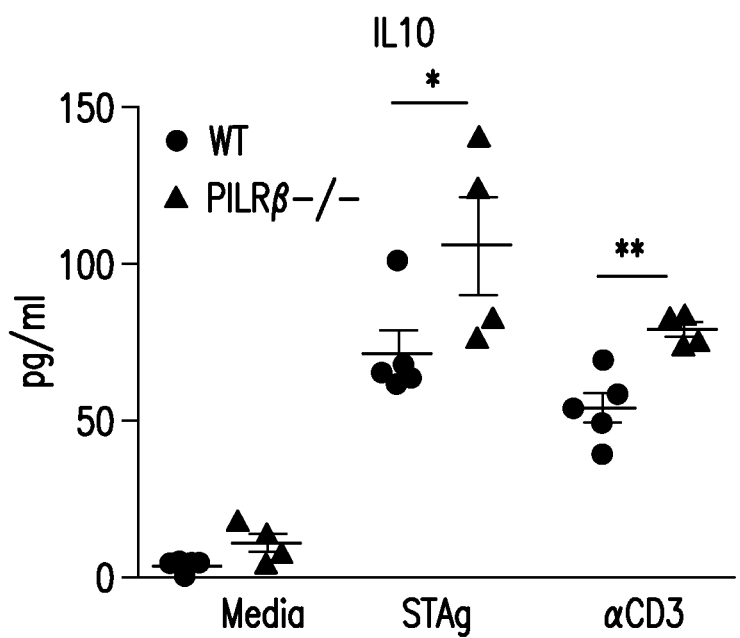

We then postulated that in the absence of PILRβ, there may be altered priming of T cell populations, resulting in the production of more IL-10 by effector T cells and therefore better control of immune pathology. IL-10 production was analyzed by both flow cytometry for intracellular cytokine staining ex vivo and by ELISA after restimulation in culture. While no differences in the percentage of IL-10 producing cells were observed by FACS analysis (data not shown), there were significantly higher levels of T cell dependent IL-10 protein production by PILRβ–/– splenocytes at day 7 than by WT cells (FIG. 5C). By day 10 post-infection, antigen-specific and TCR mediated IL-10 production in splenocyte cultures was higher in KO cultures than in WT cultures (FIG. 5D). Together these data provide evidence that absence of PILRβ results in a net increase of IL-10 production by effector T cells, which promotes survival after lethal infection. These results are consistent with previously published work on IL-10 conferring resistance to intestinal necrosis during high does *T. gondii* infection (14). Importantly, since PILRβ is not expressed on T cells, the change in cytokine production is indirectly mediated by this receptor. It was therefore proposed that there must be a change in the APC-T cell interaction, either because of altered cytokine production and/or a cell contact-dependent mechanism, that is responsible for greater IL-10 production.

Interleukin 27 (IL-27) is a member of the IL-12 family of cytokines and comprises a heterodimeric complex of EBi3 and a unique p28 subunit. IL-27 has been shown to induce IL-10 production, and thus downregulating Th17 and Th1-mediated immune pathologies. Diveu et al. (2008) *Curr. Op. Immunol.* 20:663. IL-27 has been proposed for treatment of MS. Fitzgerald & Rostami (2009) *Expert Opin. Biol. Ther.* 2009 9:149. IL-27, as well as other agonists of TCCR, have been proposed for treatment of MS and RA, as well as allograft rejection, autoimmune thyroid disease, autoimmune uveoretinitis, giant cell arteritis, inflammatory bowel disease, insulin-dependent diabetes mellitus, pernicious anemia, psoriasis, sarcoidosis, scleroderma and systemic lupus erythematosus. U.S. Pat. App. Pub. No. 2006/0177436 A1 (to Genentech).

Figure 6A:
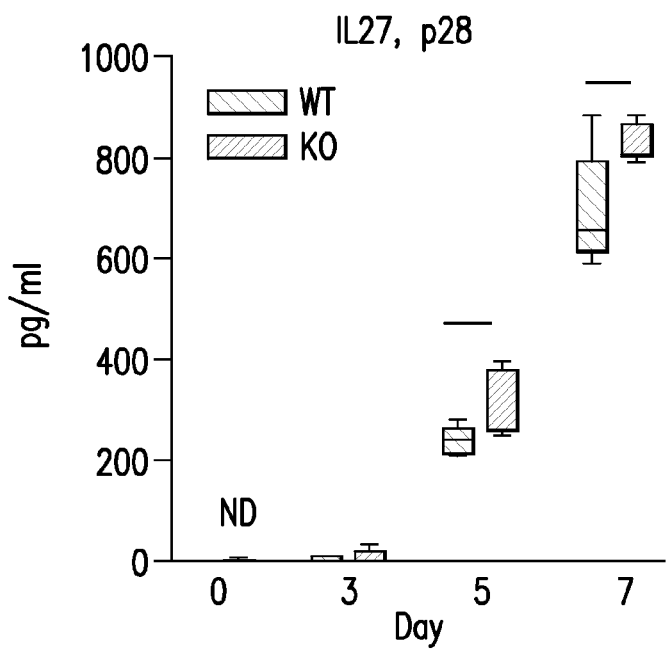
FIGS. 6A and 6B show IL-27p28 production in serum from WT and PILRβ–/– IBD mice as a function of time after per-oral infection with high dose *T. gondii*. IL-27p28 was detected by ELISA. The mean±SD is shown. Values between strains on days 5 (p=0.0219), 7 (p=0.0318), 10 (p=0.0189) and 14 (p=0.0214) are all significantly different. See Example 7.
Figure 6B:
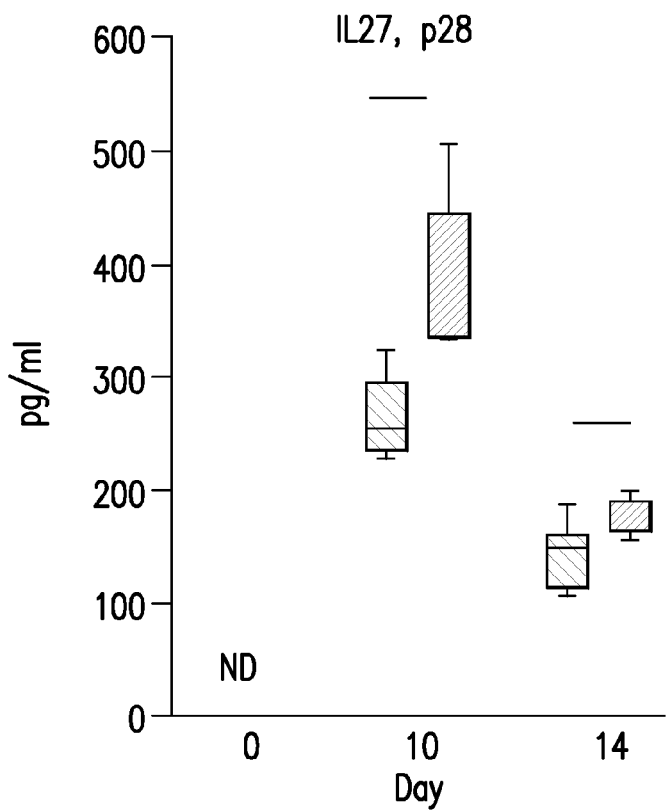
Figure 6C:
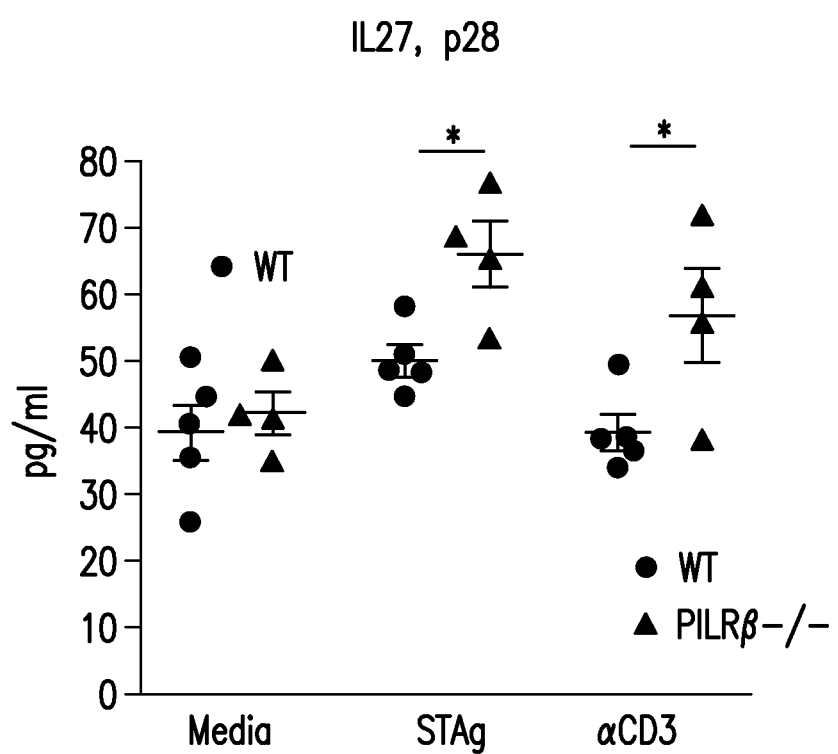
FIG. 6C shows IL-27p28 levels in the supernatant of cultures of draining lymph nodes removed from WT (circles) and PILRβ–/– (triangles) mice at day 5 post-challenge, and cultured in recall assays for 3 days. IL-27p28 was determined by p28 ELISA. Mean±SE are shown, p values<0.04. Specifically, for STAg, p=0.0143; for αCD3, p=0.0371. See Example 7.

It has been shown in the literature that the presence of IL-27 can directly induce a strong regulatory effect on CD4+ T cell production of pro-inflammatory cytokines, an effect mediated in large part by also enhancing IL-10 production (15-17) (18) (19). Thus, we assessed the production of IL-27 in WT and PILRβ deficient mice after peroral infection. Surprisingly, we found that IL27p28 levels were increased by day 7 in PILRβ–/– mice compared to WT, and this trend of higher p28 production in the KO mice was maintained through day 10 and 14 post infection (FIGS. 6A and 6B). Additionally, when mesenteric lymph nodes were cultured after 5 days of infection, IL-27p28 production in response to both antigen or αCD3 stimulation was again increased the absence of PILRβ compared to WT (FIG. 6C). The data presented at FIG. 6C suggest that in the absence of the activating receptor, increased production of IL-27p28 by macrophages and/or dendritic cells (DCs) at the local site of inflammation and in the spleen allows for enhanced resistance to lethal immunepathology. These data also suggest that PILRα and PILRβ may regulate IL-27 production by APCs.

Figure 7A:
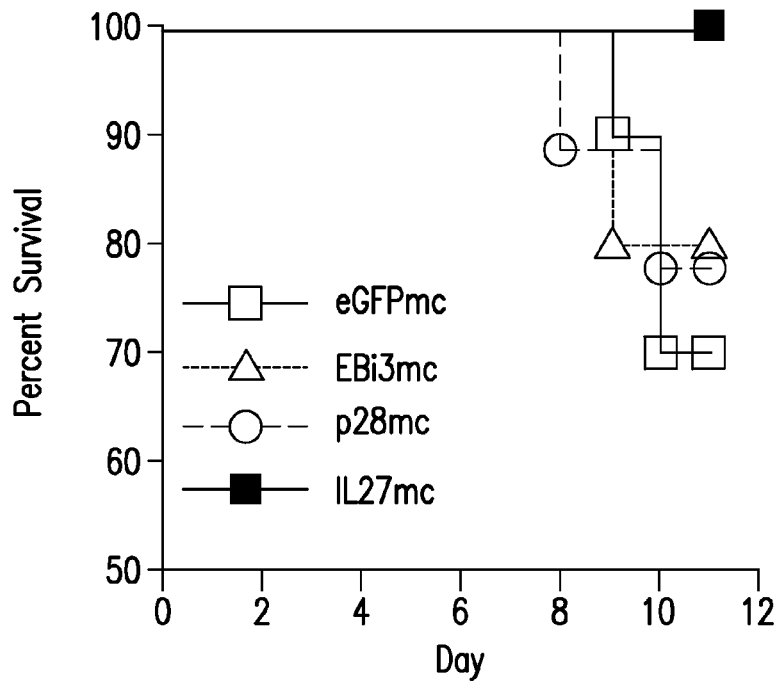
FIG. 7A shows survival of WT IBD mice at various time-points after disease induction as a function of administration of DNA minicircles ("mc") for systemic expression of eGFP, EBi3, IL-27p28 or IL-27 (as indicated) prior to high dose peroral infection with *T. gondii*. See Example 7.
Figure 7B:
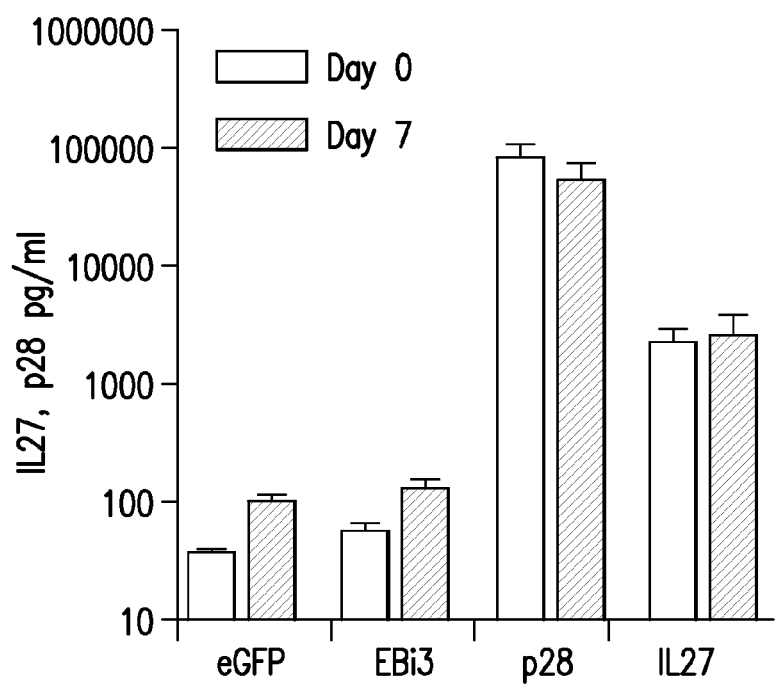
FIGS. 7B-7D show serum cytokine expression (IL-27p28, IL-10 and IFNγ, respectively) as determined by ELISA at day 0 (white bars) and day 7 (hatched bars) post infection as a function of which minicircle construct was added (eGFP, EBi3, IL-27p28 or IL-27). For FIG. 7D, means±SD are shown. See Example 7.
Figure 7C:
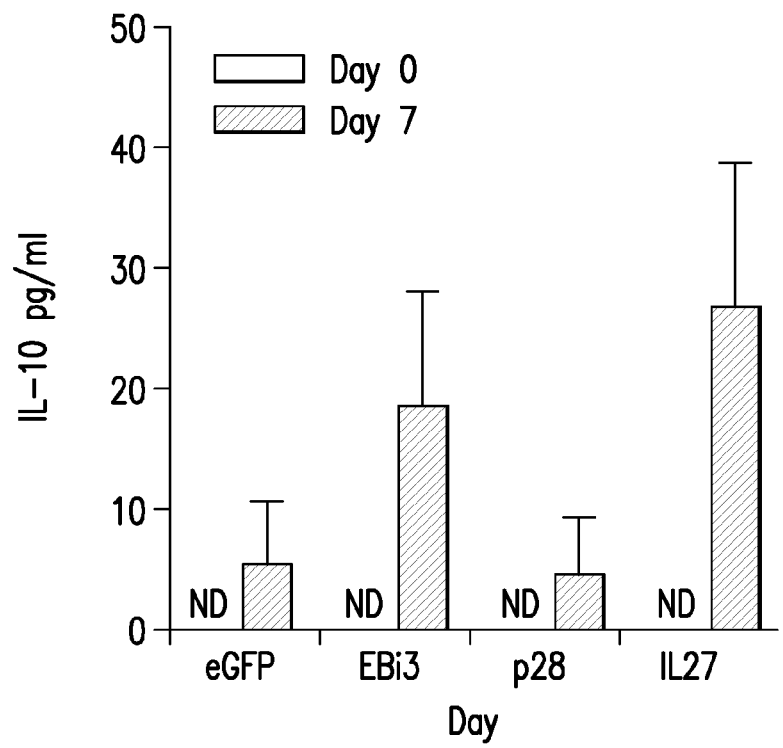

Because it is only possible to detect p28 protein in serum and supernatant samples, we wanted to ask if it was indeed the IL-27 heterodimeric complex, and not p28 alone, that mediated enhanced resistance to infection in the PILRβKO mice. In order to show this, we used minicircle technology to over express either p28, EBi3 or a linked hyperkine form of IL-27 protein in C57Bl/6 mice before high dose peroral pathogen challenge. The results presented in FIG. 7A, and discussed at Example 7, indicate that the heterodimeric IL-27 complex, and not p28 alone, is required to mediate resistance to lethal immune pathology after challenge with *T. gondii*. Although serum levels of p28 were over a log higher in p28mc mice than IL-27mc mice, p28 protein was nonetheless significantly higher than in control mc groups (eGFP and EBi3) (FIG. 7B). Consistent with previous data, we also observed a greater induction of IL-10 in the serum of IL-27mc mice by day 7 post-infection compared to control or p28mc mice (FIG. 7C). In addition, while systemic IFNγ protein was similar between the eGFPmc and p28mc groups, it was significantly reduced in the IL-27mc mice, also in agreement with previously observed in vivo data (FIG. 7C). Taken together these data provide evidence for a direct link between IL-27 (rather than p28 alone), the promotion of IL-10, and the enhanced survival of mice after parasite challenge.

Figure 8A:
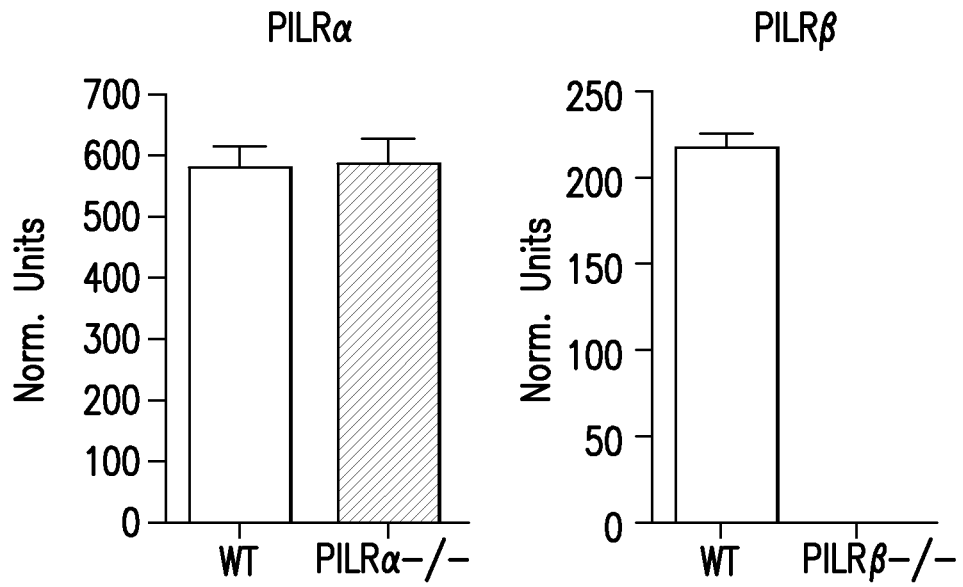
FIGS. 8A-8D show results obtained in a mouse model of immune mediated CNS inflammation caused by chronic infection ("encephalitis mice").
Figure 8B:
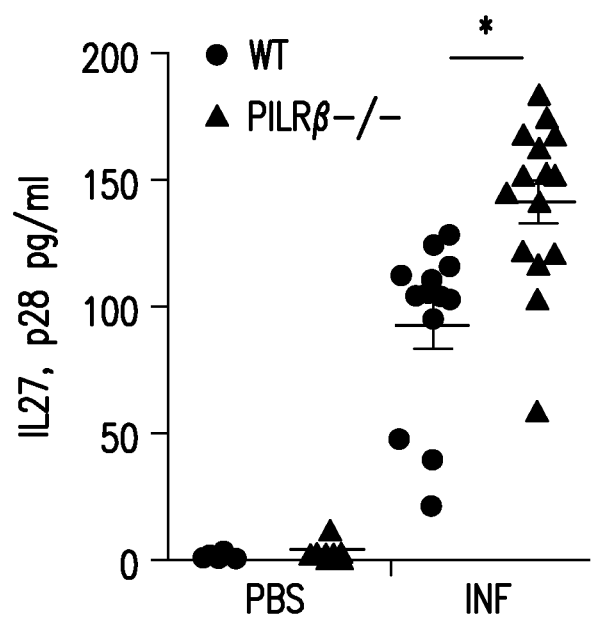
Figure 8C:
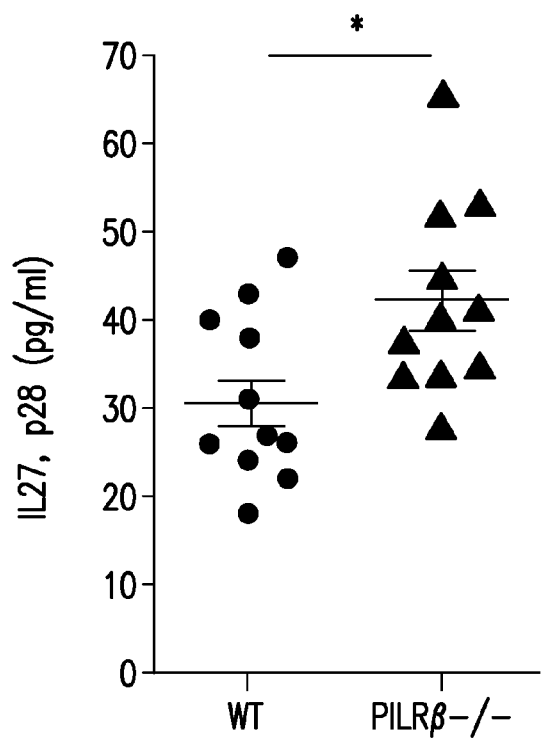
Figure 8D:
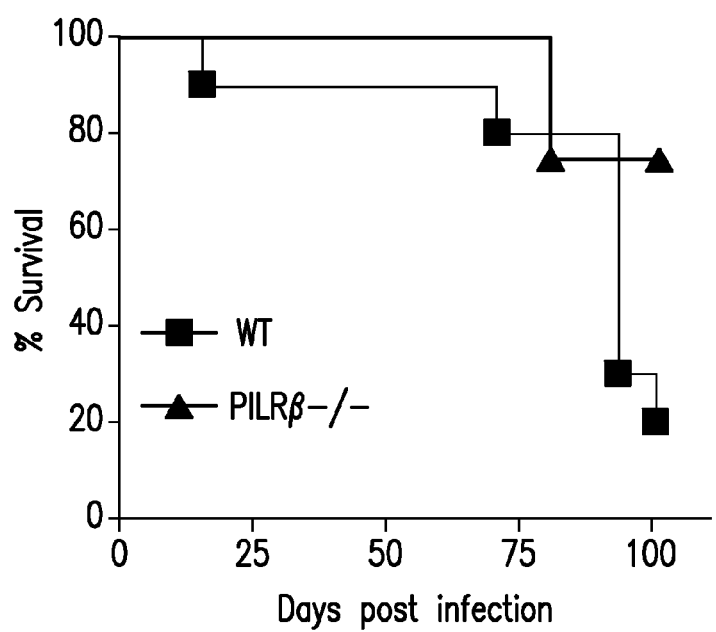

In order to test whether PILRβKO mice would also have increased resistance to toxoplasmosis (CNS inflammation), mice were infected i.p. and allowed to progress into the chronic stage of infection. Previous studies in the lab have shown increased message expression of both inhibitory and activation PILR receptors in microglial cells during EAE. To see if there was also increased expression of PILRα/β during toxoplasmosis, BMNCs were harvested from chronically infected mice and analyzed by RT-PCR for receptor message. Both WT and KO mice exhibited similar levels of inhibitory receptor, and as expected no activating receptor message was present in PILRβ-/- mice (FIG. 8A). Production of IL-27p28 was maintained throughout the course of infection (FIGS. 8B and 8C). FIG. 8D shows that while WT BL/6 mice succumb to encephalitis between 60 and 90 days post infection, PILRβ-/- mice remained significantly resistant beyond 100 days post infection. These data are evidence that the differential expression of these paired receptors can directly affect resistance to encephalitis.

These results with PILRβKO mice are consistent with the anti-FDF03/PILR antibody studies herein in EAE, which showed a decrease in disease after ligation (agonism) of the inhibitory receptor (PILRα). See, e.g., FIGS. 1 and 3.

Figure 9A:
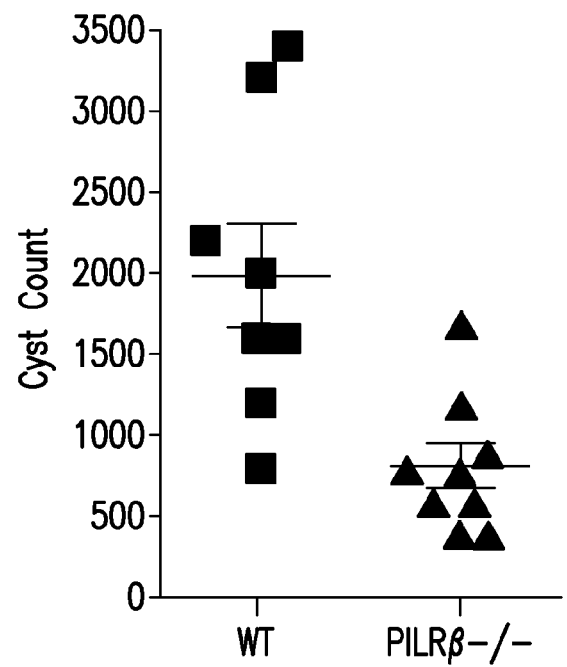
FIG. 9A shows parasite burden in brain, as measured by cyst count, in WT (squares) and PILRβ–/– (triangles) encephalitis mice. Pooled data from two experiments are shown, p=0.0033.
Figure 9B:
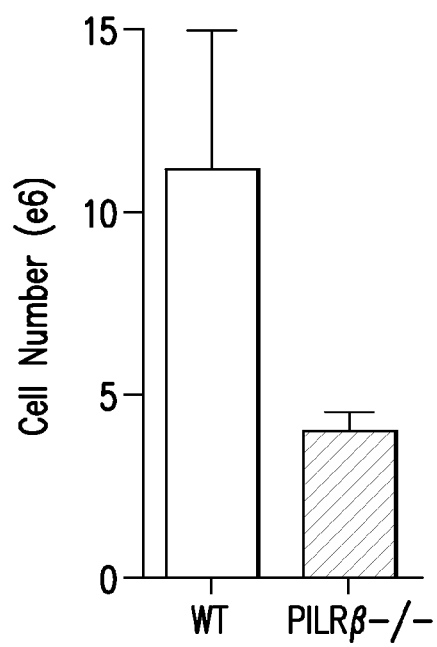
FIG. 9B shows actual cellular infiltrate in BMNCs from whole brains from WT and PILRβ–/– encephalitis mice. One representative experiment of two is shown, p=0.0471.
Figure 9C:
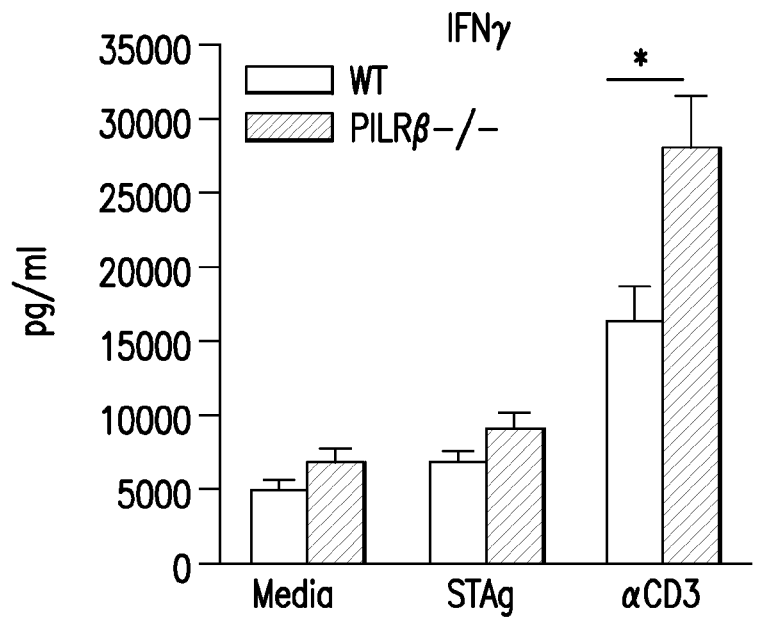
FIGS. 9C and 9D show IFNγ and IL-10 levels, respectively, in recall assays with BMNCs from WT (open bars) and PILRβ–/– (hatched bars) encephalitis mice. Pooled data from three experiments are shown. See Example 8.
Figure 9D:
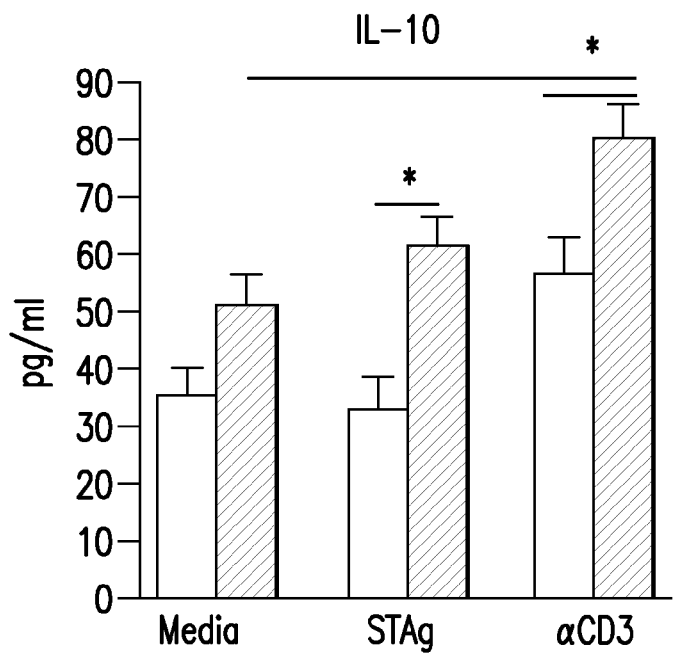

In order to investigate the mechanism behind this enhanced survival, either whole brain or BMNCs were isolated from both WT and PILRβ-/- encephalitis mice 60 days post-infection, and parasite burden and inflammatory infiltrate were quantified. Cyst counts revealed significantly lower pathogen load in the activating receptor KO mice compared to WT controls (FIG. 9A). When BMNCs were isolated from chronically infected mice and examined by flow cytometry, KO mice had significantly fewer BMNCs, consistent with enhanced resistance to encephalitis in this group (FIG. 9B). Furthermore, histological sections of brain confirmed the presence of more inflammatory foci in WT brain sections than in PILRβ-/- brains (images not shown). Chronic resistance to toxoplasmosis is a delicate balance between pro-inflammatory cytokines like IFNγ and TNFα and regulatory cytokines like IL-10 (20). Therefore, BMNCs were isolated from chronically infected mice and restimulated in a recall assay in order to determine if there was a difference in cytokine production. Paradoxically, in response to αCD3 restimulation there was significantly more TNFα (data not shown) and IFNγ in the supernatants of PILRβ-/- cultures than in WT cultures (FIG. 9C). One would have expected more inflammatory cytokine production in WT cultures given that WT mice have a higher parasite burden than PILRβ-/- mice at the same time-point. More IFNγ production in PILRβ-/- mice would also suggest the presence of more inflammatory cells, whereas FIG. 9B revealed fewer cells infiltrating the CNS. One explanation for this paradox is that the enhanced IFNγ production in PILRβ-/- mice may lead to better control of parasite reactivation, and thus better control of parasite numbers. Significantly higher IL-10 levels were detected in PILRβ-/- BMNC cultures, as compared with WT, not only in response to αCD3, but also after antigen restimulation (FIG. 9D). These data again suggest that PILRβ-/- APCs promote IL-10 secreting T effector cells that home to the CNS and provide a more stringent regulation of inflammation in the CNS.

Figure 10A:
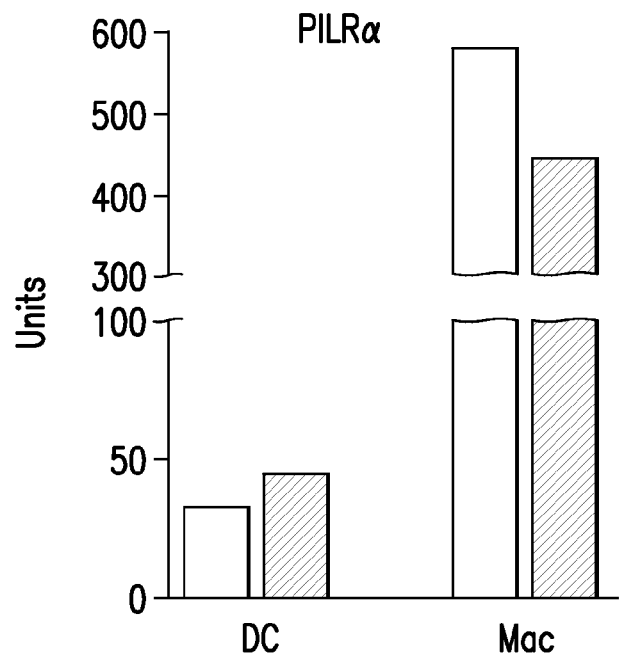
FIGS. 10A-10E present data characterizing dendritic cells (DC) and macrophages (Mac) from WT (white bars) and PILRβ–/– (hatched bars) encephalitis mice on day 5 post-infection. DCs and macrophages were sorted from individual spleens and analyzed for mRNA levels by RT-PCR.
Figure 10B:
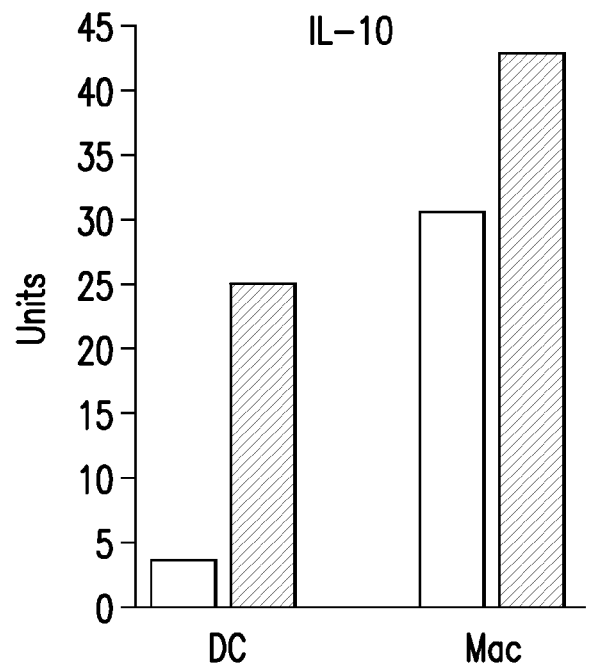
Figure 10C:
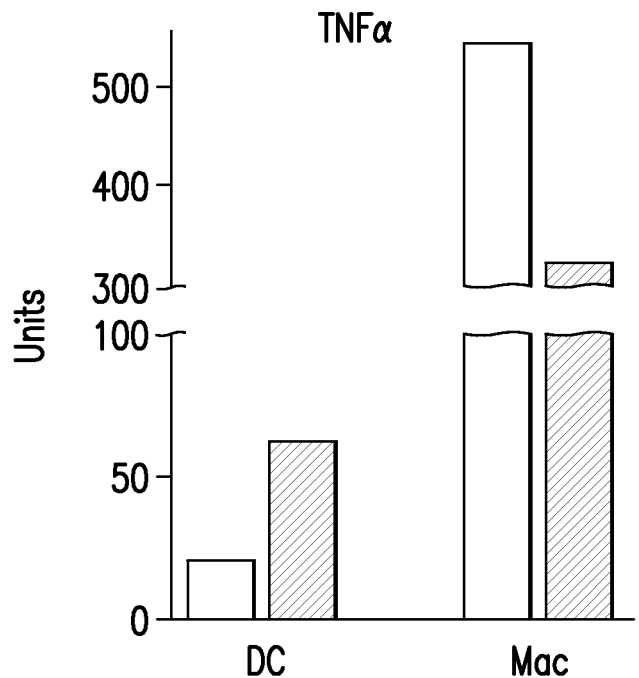
Figure 10D:
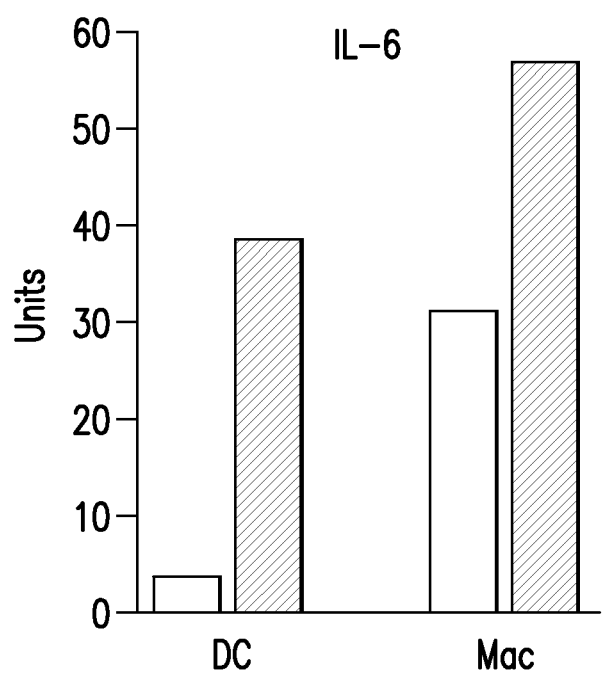
Figure 10E:
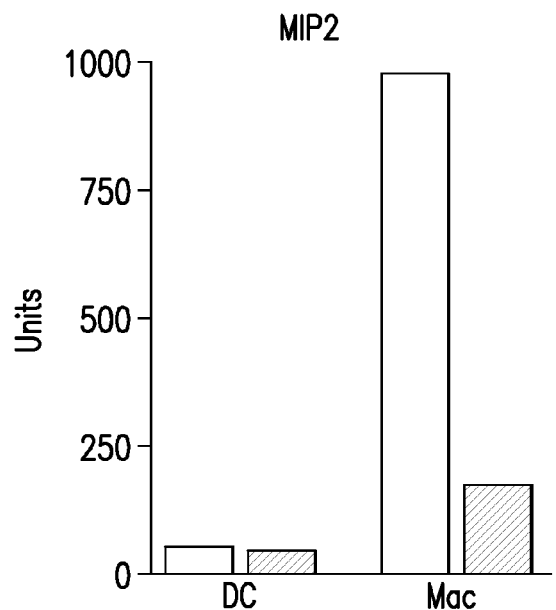
Figure 10F:
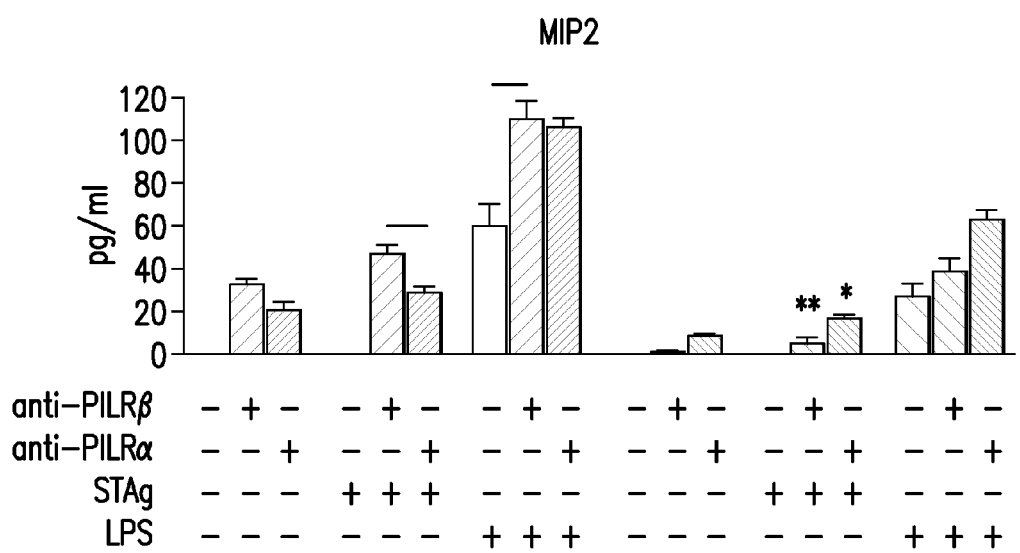
FIG. 10F shows MIP2 as detected by ELISA in supernatants of sorted macrophages, obtained from encephalitis mice, that had been cultured overnight with control antibody, or with plate-bound antibody for the activating (PILRβ) or the inhibitory (PILRα) receptor. Cultures were unstimulated or stimulated with STAg or LPS. Data using WT cells are presented in the left half of FIG. 10F, whereas data obtained using PILRβ–/– mice are shown on the right half of FIG. 10F. *p=0.0162; **p=0.0012.

Since PILRβ is expressed on many myeloid subsets, experiments were performed to identify which cells were the main source of IL-27p28 in our model. RT PCR of splenic DCs and macrophages isolated after parasitic challenge revealed similar levels of PILRα message in WT and PILRβ-/- mice (FIG. 10A), suggesting no compensatory upregulation of the inhibitory receptor in the absence of the activating receptor for either DCs or macrophages. Expression of TNFα was elevated in PILRβ-/- DCs, and expression of IL-6 and IL-10 were greater in PILRβ-/- DCs and macrophages, compared with cells from WT mice (FIGS. 10B-10D). These results suggest that by producing higher levels of IL-27, the DC population may be able to influence the strength of the inflammatory response despite high levels of inflammatory cytokines. Interestingly, expression of MIP2, which is an important pro-inflammatory chemokine produced by macrophages to promote cellular recruitment to target tissues, was lower in PILRβ-/- macrophages compared to WT macrophages (FIG. 10E), suggesting that the macrophages in PILRβKO mice may not be activated to the same level as those from WT mice after challenge. In addition to the observed reduction in MIP2 mRNA, MIP2 protein was reduced in PILRβ-/- mice compared to WT, even under culture conditions that should be largely independent of PILR ligation, such as during LPS restimulation (FIG. 10F).

Figure 10G:
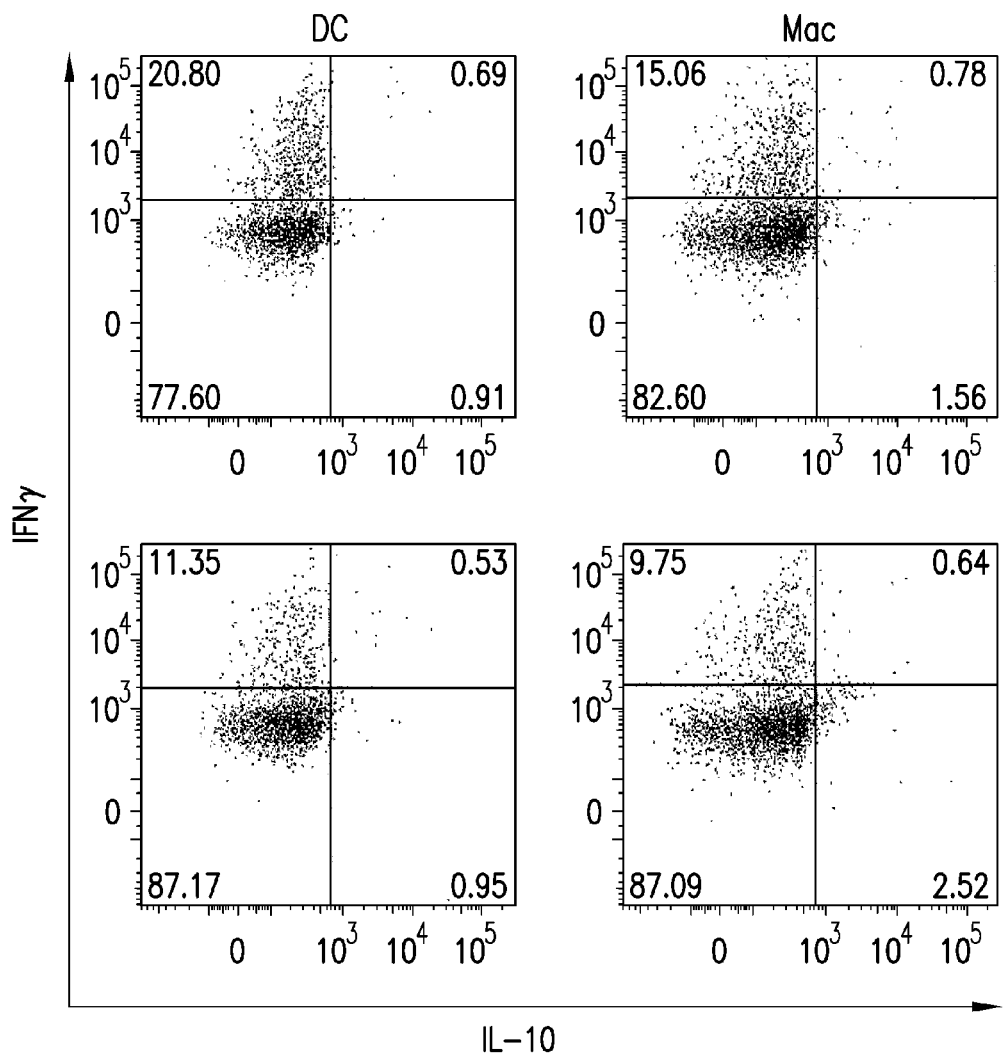
FIG. 10G shows intracellular staining of IL-10 and IFN-γ in CD4+T cells stimulated by either DCs or macrophages from WT or PILRβ–/– mice. See Example 9.

In order to see if these APC populations could directly affect the priming of T cells, mixing experiments were performed with in vivo primed APCs and T cells from OTII Tg mice. Although IL-10 was overall very low in all samples, a higher percentage of IL-10+ T cells was produced when co-cultured with PILRβ-/- macrophages (FIG. 10G, right panels). Additionally, the percentage of IFNγ+ CD4 T cells was decreased in cultures with either DC or macrophages from PILRβ-/- mice (FIG. 10G, left panels). These data reveal that when PILRβ signaling is abrogated, DCs and macrophages become more tolerogenic in phenotype by producing significantly more IL-27p28, and in turn promoting IL-10 production by T cells. The observation that PILRβ deficient DCs and macrophages induce CD4+ T cell populations expressing less IFNγ, and more IL-10, is consistent with other observations herein that PILRβ deficiency results in a more tolerogenic phenotype.

The results presented herein, when taken as a whole, suggest that agonists of PILRα, or antagonists of PILRβ, will find use in suppressing undesired immune responses, such as inflammatory responses. Agonist anti-PILRα antibody studies (FIGS. 1 and 3) show reduction of clinical score in mouse models of MS and RA. Experiments using a PILRβ−/− strain of mice also demonstrate that antagonism of PILRβ (i.e. its genetic ablation) result in increased survival in mouse models of IBD and MS (i.e. gut and CNS inflammation) (FIGS. 4A and 8D). Various other experiments demonstrate that this protective effect is the result of the anti-inflammatory effects of increased IL-27 and IL-10 production under PILRα agonist/PILRβ antagonist conditions. Such results strongly suggest that PILRα agonism/PILRβ antagonism would be useful in treatment of CNS, joint and gut inflammation, or other circumstance where the anti-inflammatory effects of IL-27 and/or IL-10 would be beneficial.

VI. Discussion of Results Obtained Using Antagonists/KO of PILRβ or Agonists of PILRα

Previously published work has identified IL-27 as having a significant influence on the balance between an effective immune response and curbing of immune pathology (21). IL-27 produced by myeloid cells has been shown not only to promote Th1 responses during an acute response to infection, but also to be required for damping of effector cell responses during late adaptive stage of infection once the pathogen is controlled (16, 22-24). The pleiotropic effects of IL-27 are also evident in the data presented here. Despite a decrease in systemic IFNγ production after i.p. challenge, PILRβ deficient mice had no issue clearing the parasite from the local site of infection. Importantly, systemic IL-10 production was not different at this early time point, and probably due to the later kinetics of T-cell derived IL-10. When activated T cells were restimulated with either antigen or αCD3, they were capable of enhanced IFNγ as well as IL-10 production. This combination provides for adequate protection against the parasite during acute infection while sustaining tight regulation of the chronic inflammatory response in the CNS. We have shown that PILRα and PILRβ are expressed not only on inflammatory macrophages and DCs, but also CNS resident cells such as microglial cells. Interestingly it is already known that cells native to the CNS, such as microglia and astrocytes produce IL-27 under some conditions of inflammation (25-27). These expression data, along with our observations that the systemic responses are not greatly altered in KO mice after challenge, may suggest that PILRα and PILRβ primarily play a role in regulating local inflammatory responses.

This control or regulation of inflammation is also highlighted in the ability of PILRβ−/− mice to survive high dose peroral infection. Susceptibility in this case is the result of immune mediated destruction of the mucosa by IFNγ-secreting CD4+ T cells and is independent of systemic infection (28, 29). Again, while the acute, systemic response to high dose infection was not altered, the data we have presented here suggest that the absence of PILRβ significantly changes the local inflammation in the gut and allows for decreased epithelial damage and enhanced survival. Furthermore, we have gone on to show specifically that macrophages and DCs not expressing the activating receptor PILRβ produce significantly more IL-27, and seemingly switch to a more regulatory phenotype with the capacity to promote increased numbers of IL-10 secreting T effector cells.

Effector T cell responses to *T. gondii* have been shown to involved the generation of IFNγ/IL-10 double positive cells that are required for regulating the immunopathology in response to the parasite (30). As previously discussed, IL-10 production is vitally important for a limited mechanism of resistance after high-dose peroral challenge with *T. gondii*, similar to its' regulatory role in IBD. Furthermore, there is an ever-increasing body of literature showing IL-27-dependent upregulation of IL-10 as a mechanism for immune regulation. And now we show here that IL-27 secretion by DC and macrophages can be modulated through ligation of the PILRα/β receptors.

In a normal host, initial ligation of the more highly expressed PILRβ promotes activation of APCs as they migrate into target tissues during the early inflammatory response. This initial interaction pushes a proinflammatory milieu due in part to high levels of IL-12 secretion and lower levels of IL-27. As APCs become activated, they are able to increase the amount of inhibitory PILRα on their surface, and with its higher affinity for CD99, may then out-compete the activating receptor for ligand. This change may cause a corresponding change in levels of IL-27 production by APCs, and a corresponding increase in IL-10 production by activated T cells at the site of inflammation and serving to downregulate the inflammatory response. Thus, PILRα provides a negative feedback loop for the activating effects of PILRβ.

Related to its suppressive affects on Th17 cells it has been recently shown that IL-27 can ameliorate inflammation and pathology associated with experimental autoimmune encephalomyelitis (EAE) and collagen induced arthritis (CIA), murine models of multiple sclerosis and rheumatoid arthritis (31-34). We provide evidence herein, for the first time, that the PILRα/β receptor pair directly promote a more tolerogenic phenotype, and thus that the appropriate agonists and antagonists may find use in altering the local proinflammatory environment in the mucosa, CNS, joint and other tissues.

VII. Anti-PILR Antibodies

Any suitable method for generating monoclonal antibodies that specifically bind to human PILRα or PILRβ may be used. For example, a non-human animal may be immunized with human PILRα or PILRβ or a fragment thereof. Any suitable method of immunization can be used. Such methods can include adjuvants, other immunostimulants, repeated booster immunizations, and the use of one or more immunization routes. Any suitable source of PILR can be used as the immunogen for the generation of the antibody of the compositions and methods disclosed herein. Such forms include, but are not limited whole protein, peptide(s), and epitopes generated through recombinant, synthetic, chemical or enzymatic degradation means known in the art. In preferred embodiments the immunogen comprises the extracellular portion of PILR.

Any form of the PILR can be used to generate the antibody. The eliciting antigen may be a single epitope, multiple epitopes, or the entire protein, alone or in combination with one or more immunogenicity enhancing agents known in the art. The eliciting antigen may be an isolated full-length protein or just the extracellular domain. The antigen may be produced in a genetically modified cell. Vectors suitable for transformation of the cells of interest include viruses and plasmids, or DNA may be introduced directly to cells using cationic lipids.

Any suitable method can be used to elicit an antibody with the desired biologic properties to modulate PILR signaling. It is desirable to prepare monoclonal antibodies (mAbs) from various mammalian hosts, such as mice, rats, other rodents, rabbits, humans, other primates, etc. Description of techniques for preparing such monoclonal antibodies may be found in, e.g., Stites et al. (eds.) BASIC AND CLINICAL IMMUNOL- OGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a antigen binding fragment thereof by screening a DNA library from human B cells according, e.g., to the general protocol outlined by Huse et al. (1989) *Science* 246:1275-1281.

Other suitable techniques involve selection of libraries of antibodies in phage or similar vectors. See, e.g., Huse et al. supra; and Ward et al. (1989) *Nature* 341:544-546. Recombinant immunoglobulins may be produced. See Cabilly U.S. Pat. No. 4,816,567; and Queen et al. (1989) *Proc. Nat'l Acad. Sci. USA* 86:10029-10033; or made in transgenic mice, see Mendez et al. (1997) *Nature Genetics* 15:146-156. See also Abgenix and Medarex technologies.

Antibodies or binding compositions against predetermined fragments of PILR can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective PILR. These monoclonal antibodies will usually bind with at least a $K_d$ of about 1 μM, more usually at least about 300 nM, 30 nM, 10 nM, 3 nM, 1 nM, 300 pM, 100 pM, 30 pM or better, usually determined by ELISA.

Exemplary non-human sources for antibody hypervariable regions (CDRs) include murine (e.g. *Mus musculus*), rat (e.g. *Rattus norvegicus*), Lagomorphs (including rabbits), bovine, and non-human primates. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate, having the desired properties. In some instances, Fv framework region (FR) residues of the human immunoglobulin are replaced by corresponding non-human residues from the donor antibody. Furthermore, humanized antibodies may comprise residues that are not found in the recipient antibody or in the donor antibody. These modifications are made to further refine antibody performance or improve the desired biological activity. For further details, see Jones et al. (1986) *Nature* 321:522-525; Reichmann et al. (1988) *Nature* 332:323-329; and Presta (1992) *Curr. Op. Struct. Biol.* 2:593-596.

Anti-PILR antibodies of the present invention may be screened to ensure that they are specific for only one of PILRα and PILRβ as follows. Clearly, anti-PILRα antibodies are raised using immunogen comprising PILRα, or an immunogenic fragment thereof, and anti-PILRβ antibodies are raised using immunogen comprising PILRβ, or an immunogenic fragment thereof. To confirm that the resulting anti-PILR antibodies do not cross-react with the other form of PILR, a competition ELISA may be used. See, e.g., Example 2. Briefly, the immunogen used to raise the antibody is bound to a well on a plate. Candidate antibodies are added to the wells either alone, or in the presence of varying concentrations of PILRα and PILRβ or fragments thereof. The ratio of PILRα to PILRβ necessary to achieve a given level of inhibition of binding (e.g. 50% reduction) reflects the PILRα-specificity of the candidate antibody. In the case of antibodies raised against PILRβ, or an antigenic fragment thereof, the ratio can more conveniently be expressed as the PILRβ-specificity (the ratio of PILRβ to PILRα). Non-cross-reactive anti-PILR antibodies may exhibit PILRα- or PILRβ-specificities of about two, five, ten, 30, 100, 300, 1000 or more.

Figure 1:
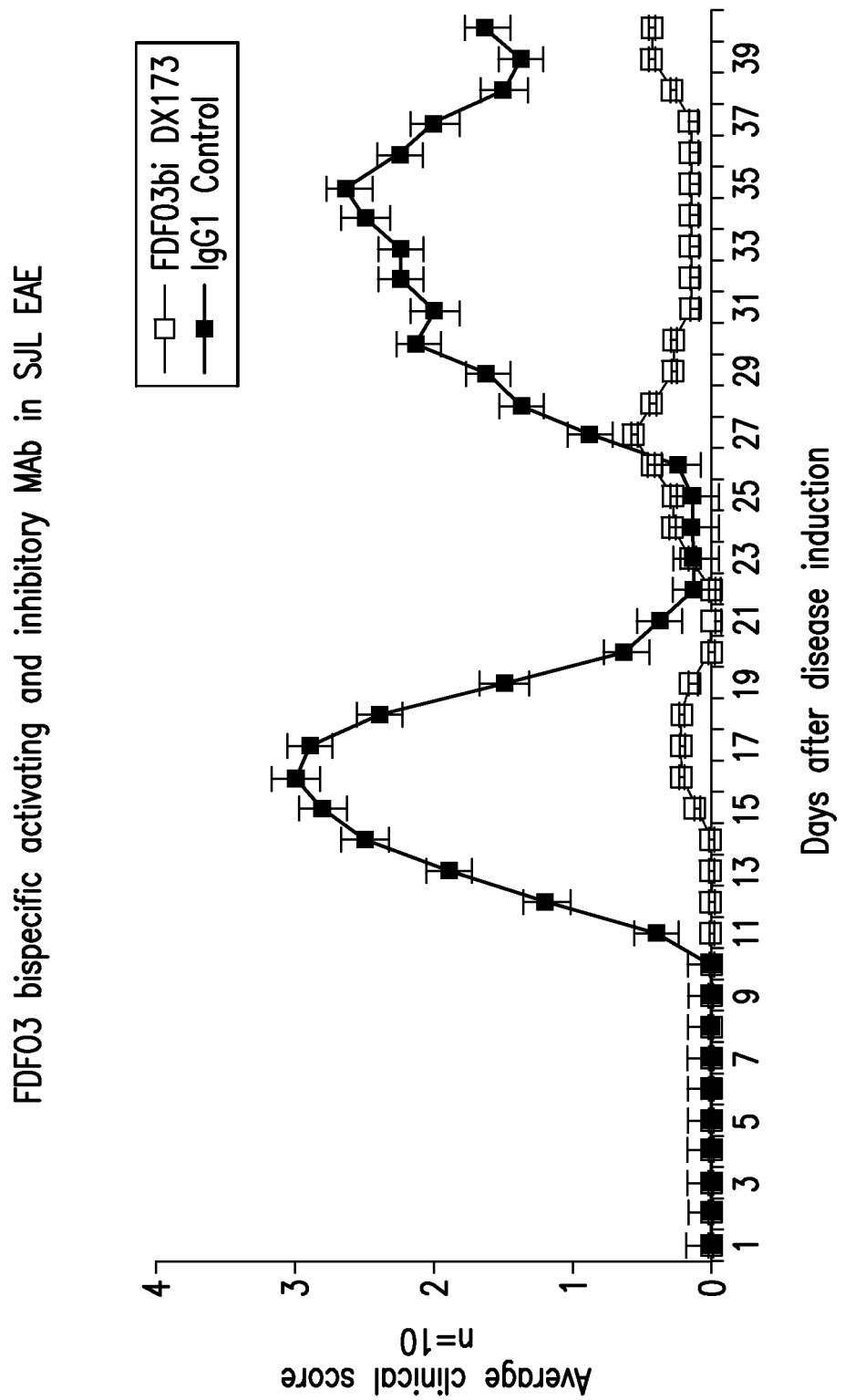
FIG. 1 shows average clinical scores in EAE mice treated with bispecific antibody "FDF03bi DX173" or an IgG1 isotype control. FDF03bi (DX173) binds to both PILR$\alpha$ and PILR$\beta$. See Example 5.

Note that it is not necessarily essential that an anti-PILR antibody be non-cross-reactive with the other form of PILR, provided that the antibody nonetheless provides therapeutic benefit. For example, FIG. 1 shows that a bispecific agonist antibody against both PILRα and PILRβ significantly reduces pathology in EAE mice. Although experiments with non-bispecific antibodies suggest that it is agonism of PILRα that is primarily responsible for the beneficial effect (FIGS. 3A and 3B), they also demonstrate that binding to PILRβ in the bispecific antibody did not negate this beneficial effect. As a result, it is apparent that a PILRα agonist need not be completely non-cross-reactive with PILRβ, since bispecific antibody DX173, which does bind to PILRβ, shows beneficial effect.

Anti-PILR antibodies may also be screened to identify antagonists of PILRβ or agonists of PILRα. One screen for PILRβ antagonists is based on use of PILRβ agonists, such as the putative natural ligand CD99 (SEQ ID NOS: 6 and 8) or agonist anti-PILRβ antibodies (e.g. DX266), to induce degranulation of mast cells. See Example 2. Accordingly, antagonists of PILRβ can be identified by screening for agents (e.g. antibodies) that block this agonist-induced degranulation. Alternatively, antagonists of PILRβ can be identified by screening for agents (e.g. antibodies) that decrease MIP-2 production in macrophages obtained from wild-type C57Bl/6 mouse spleens. See Example 9 and FIG. 10E. For example, antibodies that specifically bind to PILRβ and decrease MIP-2 expression by at least 10%, 30%, 50%, 75%, 90%, 95% or more (as measured at the protein level) are considered PILRβ antagonists.

Similarly, agonists of the inhibitory PILRα receptor can be identified based on their ability to suppress mast cell degranulation, for example degranulation induced by agonists of the activating receptor PILRβ or agonists of other activating receptors, such as CD200RL1. See Example 2. Alternatively, agonists of PILRα can be identified based on their ability to reduce antigen-specific proliferation of lymph node T cells obtained from EAE mice. See Example 5 and FIGS. 2A and 2B.

Antibodies of the present invention may also be conjugated to a chemical moiety. The chemical moiety may be, inter alia, a polymer, a radionuclide or a cytotoxic factor. Preferably the chemical moiety is a polymer that increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee et al. (1999) (*Bioconj. Chem.* 10:973-981) discloses PEG conjugated single-chain antibodies. Wen et al. (2001) (*Bioconj. Chem.* 12:545-553) disclose conjugating antibodies with PEG which is attached to a radiometal chelator (diethylenetriaminepentaacetic acid (DTPA)).

The antibodies and antibody fragments may also be conjugated with a detectable label, such as fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals. Other detectable labels include, e.g., radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

Any method known in the art for conjugating the antibody molecules of the invention to the various moieties may be employed, including those methods described by Hunter et al. (1962) *Nature* 144:945; David et al. (1974) *Biochemistry* 13:1014; Pain et al. (1981) *J. Immunol. Meth.* 40:219; and Nygren (1982) *Histochem. and Cytochem.* 30:407.

VIII. Nucleic Acid-Based Antagonists of PILRβ

An antagonist of PILRβ also includes nucleic acid-based antagonists that reduce the expression of PILRβ, such as antisense nucleic acids and siRNA. See, e.g., Arenz and Schepers (2003) *Naturwissenschaften* 90:345-359; Sazani and Kole (2003) *J. Clin. Invest.* 112:481-486; Pirollo et al. (2003) *Pharmacol. Therapeutics* 99:55-77; Wang et al. (2003) *Antisense Nucl. Acid Drug Devel.* 13:169-189. Design of such antagonists is within the skill in the art in light of the known sequence of the mRNA encoding PILRβ, which is available at NCBI Nucleic Acid Sequence Database Accession Numbers NM_013440.3, and is provided herein at SEQ ID NO: 3.

Methods of producing and using siRNA are disclosed, e.g., at U.S. Pat. Nos. 6,506,559 (WO 99/32619); 6,673,611 (WO 99/054459); 7,078,196 (WO 01/75164); 7,071,311 and PCT publications WO 03/70914; WO 03/70918; WO 03/70966; WO 03/74654; WO 04/14312; WO 04/13280; WO 04/13355; WO 04/58940; WO 04/93788; WO 05/19453; WO 05/44981; WO 03/78097 (U.S. patents are listed with related PCT publications). Exemplary methods of using siRNA in gene silencing and therapeutic treatment are disclosed at PCT publications WO 02/096927 (VEGF and VEGF receptor); WO 03/70742 (telomerase); WO 03/70886 (protein tyrosine phosphatase type IVA (Prl3)); WO 03/70888 (Chk1); WO 03/70895 and WO 05/03350 (Alzheimer's disease); WO 03/70983 (protein kinase C alpha); WO 03/72590 (Map kinases); WO 03/72705 (cyclin D); WO 05/45034 (Parkinson's disease). Exemplary experiments relating to therapeutic uses of siRNA have also been disclosed at Zender et al. (2003) *Proc. Nat'l. Acad. Sci. (USA)* 100:7797; Paddison et al. (2002) *Proc. Nat'l. Acad. Sci. (USA)* 99:1443; and Sah (2006) *Life Sci.* 79:1773. siRNA molecules are also being used in clinical trials, e.g., of chronic myeloid leukemia (CML) (ClinicalTrials.gov Identifier: NCT00257647) and age-related macular degeneration (AMD) (ClinicalTrials.gov Identifier: NCT00363714).

Although the term "siRNA" is used herein to refer to molecules used to induce gene silencing via the RNA interference pathway (Fire et al. (1998) *Nature* 391:806), such siRNA molecules need not be strictly polyribonucleotides, and may instead contain one or more modifications to the nucleic acid to improve its properties as a therapeutic agent. Such agents are occasionally referred to as "siNA" for short interfering nucleic acids. Although such changes may formally move the molecule outside the definition of a "ribo" nucleotide, such molecules are nonetheless referred to as "siRNA" molecules herein. For example, some siRNA duplexes comprise two 19-25 nt (e.g. 21 nt) strands that pair to form a 17-23 basepair (e.g. 19 base pair) polyribonucleotide duplex with TT (deoxyribonucleotide) 3' overhangs on each strand. Other variants of nucleic acids used to induce gene silencing via the RNA interference pathway include short hairpin RNAs ("shRNA"), for example as disclosed in U.S. Pat. App. Publication No. 2006/0115453.

The sequence of the opposite strand of the siRNA duplexes is simply the reverse complement of the sense strand, with the caveat that both strands have 2 nucleotide 3' overhangs. That is, for a sense strand "n" nucleotides long, the opposite strand is the reverse complement of residues 1 to (n-2), with 2 additional nucleotides added at the 3' end to provide an overhang. Where an siRNA sense strand includes two U residues at the 3' end, the opposite strand also includes two U residues at the 3' end. Where an siRNA sense strand includes two dT residues at the 3' end, the opposite strand also includes two dT residues at the 3' end.

The use of complimentary sequences to arrest translation of mRNAs was described in the late 1970s. See, e.g., Paterson et al. (1977) *Proc. Natl. Acad. Sci. (USA)* 74:4370-4374; Hastie & Held (1978) *Proc. Natl. Acad. Sci. (USA)* 75: 1217-1221 and Zamecnik & Stephenson (1978) *Proc. Natl. Acad. Sci. (USA)* 75:280-284. However, the use of antisense oligonucleotides for selective blockage of specific mRNAs is of recent origin. See, e.g., Weintraub et al. (1985) *Trends Genet.* 1:22-25 (1985); Loke et al. (1989) *Proc. Natl. Acad. Sci. (USA)* 86:3474-3478; Mulligan et al. (1993) *J. Med. Chem.* 36:1923-1937 (1993); and Wagner (1994) *Nature* 372:333-335. The mechanism of antisense inhibition in cells was previously analyzed and the decrease in mRNA levels mediated by oligonucleotides was shown to be responsible for the decreased expression of several proteins. See Walder & Walder (1988) *Proc. Natl. Acad. Sci. (USA)* 85:5011-5015; Dolnick (1991) *Cancer Invest.* 9:185-194; Crooke & LeBleu (1993) *Antisense Research and Applications*, CRC Press, Inc., Boca Raton, Fla.; Chiang et al. (1991) *J. Biol. Chem.* 266:18162-18171; and Bennett et al. (1994) *J. Immunol.* 152: 3530-3540. The use of antisense oligonucleotides is recognized as a viable option for the treatment of diseases in animals and man. For example, see U.S. Pat. Nos. 5,098,890; 5,135,917; 5,087,617; 5,166,617; 5,166,195; 5,004,810; 5,194,428; 4,806,463; 5,286,717; 5,276,019; 5,264,423; 4,689,320; 4,999,421 and 5,242,906, which teach the use of antisense oligonucleotides in a variety of diseases including cancer, HIV, herpes simplex virus, influenza virus, HTLV-HI replication, prevention of replication of foreign nucleic acids in cells, antiviral agents specific to CMV, and treatment of latent EBV infections.

An antisense nucleic acid can be provided as an antisense oligonucleotide. See, e.g., Murayama et al. (1997) *Antisense Nucleic Acid Drug Dev.* 7:109-114. Genes encoding an antisense nucleic acid can also be provided; such genes can be formulated with a delivery enhancing compound and introduced into cells by methods known to those of skill in the art. For example, one can introduce a gene that encodes an antisense nucleic acid in a viral vector, such as, for example, in hepatitis B virus (see, e.g., Ji et al. (1997) *J. Viral Hepat.* 4:167-173); in adeno-associated virus (see e.g., Xiao et al. (1997) *Brain Res.* 756:76-83; or in other systems including, but not limited, to an HVJ (Sendai virus)-liposome gene delivery system (see, e.g., Kaneda et al. (1997) *Ann. N.Y. Acad. Sci.* 811:299-308); a "peptide vector" (see, e.g., Vidal et al. (1997) *CR Acad. Sci. III* 32:279-287); as a gene in an episomal or plasmid vector (see, e.g., Cooper et al. (1997) *Proc. Natl. Acad. Sci.* (U.S.A.) 94:6450-6455, Yew et al. (1997) *Hum Gene Ther.* 8:575-584); as a gene in a peptide-DNA aggregate (see, e.g., Niidome et al. (1997) *J. Biol. Chem.* 272:15307-15312); as "naked DNA" (see, e.g., U.S. Pat. No. 5,580,859 and U.S. Pat. No. 5,589,466); in lipidic vector systems (see, e.g., Lee et al. (1997) *Crit. Rev. Ther. Drug Carrier Syst.* 14:173-206); polymer coated liposomes (U.S. Pat. Nos. 5,213,804 and 5,013,556); cationic liposomes (U.S. Pat. Nos. 5,283,185; 5,578,475; 5,279,833; 5,334,761); gas filled microspheres (U.S. Pat. No. 5,542,935), ligand-targeted encapsulated macromolecules (U.S. Pat. Nos. 5,108, 921; 5,521,291; 5,554,386; and 5,166,320).

IX. Pharmaceutical Compositions

To prepare pharmaceutical or sterile compositions including PILR antibodies, the antibody, or antigen-binding fragment thereof, soluble PILRα/β, CD99, or other therapeutic agent of the present invention is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984). Formulations may be prepared by mixing with physiologically acceptable carriers, excipients, or stabilizers in the form of, e.g., lyophilized powders, slurries, aqueous solutions or suspensions. See, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the therapeutic compositions of the present invention can be determined by standard pharmaceutical procedures in cell cultures or in experimental animals, e.g., for determining the $LD_{50}$ (the dose lethal to 50% of the population) and the $ED_{50}$ (the dose therapeutically effective in 50% of the population). The dose ratio between toxic and therapeutic effects (the ratio of $LD_{50}$ to $ED_{50}$) is the therapeutic index. Agents exhibiting high therapeutic indices are preferred. The data obtained from these cell culture assays and animal studies can be used in deducing a dose range for use in human subjects. The dosage is preferably within a range of circulating concentrations that include the $ED_{50}$ with little or no toxicity, i.e. comfortably below the $LD_{50}$. The dosage may vary within this range depending on the formulation and route of administration.

The mode of administration of the therapeutic agents of the present invention is not particularly important. Suitable routes of administration may, for example, include oral, pulmonary (inhalation), rectal, transmucosal, topical application or cutaneous, or intestinal administration; parenteral delivery, including intramuscular, subcutaneous, intramedullary injections, as well as intrathecal, epidural, direct intraventricular, intraarterial, intravenous, intraperitoneal, intranasal, or intraocular injections.

Alternately, one may administer the antibody in a local rather than systemic manner, for example, via injection of an antibody directly into an arthritic joint or pathogen-induced lesion, often in a depot or sustained release formulation. Intrathecal or epidural administration may be preferred for treatment of CNS inflammation, such as MS. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies, antibody fragments, and cytokines can be provided by continuous infusion, or by doses at intervals of, e.g., one day, 1-7 times per week, one week, two weeks, monthly, bimonthly, etc. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346: 1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

As used herein, the term "therapeutically effective amount" or "effective amount" refers to an amount of an PILR-specific binding compound, e.g. and antibody, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, antibody, steroid, chemotherapeutic agent, antibiotic, or radiation, are well known in the art, see, e.g., Hardman et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., PA. Antibiotics can include known antibacterial, anti-fungal, and anti-viral agents. Antibacterial agents can include, but are not limited to beta lactam agents that inhibit of cell wall synthesis, such as penicillins, cephalosporins, cephamycins, carbopenems, monobactam; and non beta lactam agents that inhibit cell wall synthesis, such as vancomycin and teicoplanin. Other antibiotics can inhibit cellular activity such as protein and nucleic acid synthesis. These agents include, but are not limited to, macrolides, tetracyclines, aminoglycosides, chloramphenicol, sodium fusidate, sulphonamides, quinolones, and azoles.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning, 3rd ed.*, Cold Spring Harbor Laboratory Press, Cold Spring Harbor, N.Y.; Wu (1993) *Recombinant DNA*, Vol. 217, Academic Press, San Diego, Calif. Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science, Vol. 2*, John Wiley and Sons, Inc., New York; Ausubel et al. (2001) *Current Protocols in Molecular Biology, Vol. 3*, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protocols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protocols in Immunology, Vol. 4*, John Wiley, Inc., New York.

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry, 2nd ed.*; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) *Catalogue*, Molecular Probes, Inc., Eugene, Oreg.; Sigma-Aldrich (2003) *Catalogue*, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, MD); GCG Wisconsin Package (Accelrys, Inc., San Diego, CA); DECYPHER® (TimeLogic Corp., Crystal Bay, Nevada); Menne et al. (2000) Bioinformatics 16: 741-742; Menne et al. (2000) Bioinformatics Applications Note 16:741-742; Wren et al. (2002) Comput. Methods Programs Biomed. 68:177-181; von Heijne (1983) Eur. J. Biochem. 133:17-21; von Heijne (1986) Nucleic Acids Res. 14:4683-4690.

*T. gondii* cysts were used to induce inflammation in mice, as described in Examples 7 and 8, infra. For in vivo experiments, mice were inoculated either intra-peritoneally with 20 cysts (encephalitis model) or per orally with 80-100 cysts (IBD model) of the Me-49 strain of *T. gondii*. Brain homogenate from chronically infected CBA/CaJ mice (Jackson Labs) were used as the source of cyst preparations for inoculation.

When needed, brain mononuclear cells (BMNC) were isolated from the CNS by performing collagenase digestion and separating lymphocyte populations using a percoll gradient as previously described (35, 36). Cells were plated at $2\times10^5$ cells per well in complete RPMI (Life Technologies, Gaithersburg, Md.) supplemented with 10% FCS (HyClone Laboratories, Logan, Utah), 1% HEPES, 5004 2-mercaptoethanol, 1% sodium pyruvate, and penicillin and streptomycin for a final volume of 200 ul. Cultures were stimulated with either αCD3 at 5 µg/ml or soluble *Toxoplasma* antigen (STAg) at 20-25 µg/ml (generous gift of C. A. Hunter, University of Pennsylvania, Philadelphia, Pa.).

Splenocyte and lymph node (LN) cells were cultured as follows. Spleens or LNs were harvested and dissociated into single-cell suspensions in complete RPMI. Erythrocytes were depleted from splenocyte suspensions using RBC Lysing Buffer (Sigma, St. Louis, Mo., USA), and cells were washed in complete media. Cells were plated at either $4 \times 10^5$ or $2 \times 10^5$ cells per well for splenocytes or LNs, respectively, and for a final volume of 200 µl. Cells were cultured as above for analysis of cytokine production after 2-3 days of restimulation at 37° C.

Flow cytometry for intracellular cytokine staining was performed as follows. Cells were stimulated with 50 ng/ml PMA and 500 ng/ml ionomycin (both Sigma-Aldrich) in the presence of Golgi-plug (BD Biosciences) for 4 hours in complete medium. Surface staining was then performed in the presence of Fc-blocking antibodies, followed by intracellular staining for IFNγ, and IL-10 using the cytofix-cytoperm kit (BD Biosciences) as directed. All antibodies were purchased from BD Biosciences (San Jose, Calif., USA). All samples were collected using Canto II (BD Biosciences) and data were analyzed using FlowJo software (Tree Star, San Carlos, Calif., USA).

Antigen presenting cells (APCs) were enriched as follows. Magnetic cell sorting was performed to enrich populations of splenic dendritic cells (CD11c (N418) microbeads) and macrophages (CD11b microbeads), respectively from mice 5 days post i.p. parasite or PBS challenge using the standard protocols from Miltenyi Biotec (Auburn, Calif., USA). Cells were sorted using an autoMacs Separator and then cultured at $1 \times 10^6$ cell per well on plates previously coated with activating antibodies for PILRα, PILRβ or rIgG1 control. APCs were then stimulated with either STAg or LPS (1 ng/ml) (Sigma) for 20 hrs prior to supernatant collection and analysis for cytokine protein.

Gene expression from tissues was measured as follows. Total RNA was extracted from dissected tissue by homogenizing organs into RNA STAT-60 (Tel-Test) using a polytron homogenizer, and following manufacturer's instructions. After isopropyl alcohol precipitation, total RNA was re-extracted with phenol:chloroform:isoamyl alcohol (25:24:1) (Sigma-Aldrich, St. Louis, Mo., USA) using phase-lock light tubes (Eppendorf, Hauppauge, N.Y., USA). For cell pellets, RNA was isolated using the RNeasy method, according to the manufacturer's protocol (Qiagen Inc., Valencia, Calif., USA). Total RNA was reverse-transcribed using QuantiTect (Quiagen Inc., Valencia, Calif., USA) according to manufacturer's instructions. Primers were obtained commercially from Applied Biosystems (Foster City, Calif., USA). Real-time quantitative PCR was performed using an ABI 7300 or 7900 sequence detection system. The absence of genomic DNA contamination was confirmed using primers that recognize genomic region of the CD4 promoter. Quantities of transcripts encoding ubiquitin were measured in a separate reaction and used to normalize the data by the –Ct method (39).

Student's t-test was performed for analysis of significance and all results are expressed as mean±SEM, unless otherwise noted. P values are presented where statistical significance was found.

Example 2

Generation and Characterization of Anti-FDF03/PILR Antibodies

Agonist antibodies against the activating PILRβ and inhibitory PILRα for both human and mouse were generated in-house as described previously (see, e.g., Fournier, et al. supra). Briefly, female Lewis rats were immunized at regular intervals with a fusion protein consisting of the extracellular domain of mouse or human PILRα/β gene fused to the Fc domain of hIg as described previously (Wright et al. (2003) *J. Immunol.* 171:3034-3046). Hybridomas were initially selected that recognized PILRα/β-Ig (but not the control Ig) fusion protein in indirect ELISA. Hybridomas were then further selected based on their ability to recognize neutrophils, PBMCs and appropriate stably transfected mast cell lines.

Antibodies were further characterized as agonist antibodies specific for murine PILRα (DX276) or PILRβ (DX266) based on their ability to inhibit or activate degranulation (measured by (3-hexosaminidase release) in mast cell transfectants expressing PILRα (e.g. DT866) or expressing PILRβ (e.g. DT865), respectively. See Zhang et al. (2004) 173:6786 and Cherwinski et al. (2005) *J. Immunol.* 174:1348, both of which are hereby incorporated by reference. Briefly, to determine whether an antibody is a PILRβ agonist, degranulation is triggered by incubating $1 \times 10^6$ mouse mast cells with the potential PILRβ agonist antibody for one hour in RPMI 1640 medium in 96-well plates.

To determine whether an antibody was a mouse PILRα agonist, degranulation was triggered by incubating $1 \times 10^6$ mouse mast cells with an agonist antibody that binds to the activating receptor CD200RLa (DX89) for one hour in RPMI 1640 medium in 96-well plates, in the presence and in the absence of the potential PILRα agonist antibody.

For both PILRβ and PILRα agonist assays, a 20 µl sample of supernatant was then mixed with 60 µl of the β-hexosaminidase substrate p-nitrophenol-N-acetyl-β-D-glucosaminide (Sigma-Aldrich, St. Louis, Mo., USA) at 1.3 mg/ml in 0.1 M citric acid, pH 4.5. After 3-4 hours at 37° C., 100 µl of stop solution (0.2 M glycine, 0.2 M NaCl, pH 10.7) was added, and the $OD_{405-650}$ was read using a microplate reader (Molecular Devices, Sunnyvale, Calif., USA). Higher $OD_{405-650}$ reflects more β-hexosaminidase in the supernatant, which in turn reflects enhanced degranulation of the mast cells being assayed. See also U.S. Pat. App. Pub. No. 20030223991.

An antibody that specifically binds to mouse PILRβ and triggers degranulation in mast cell transfectants expressing PILRβ (such as DT865), as measured by β-hexosaminidase release, is an agonistic anti-PILRβ antibody. Such data are and particularly reliable if degranulation is triggered in a concentration-dependent manner.

Similarly, an antibody that specifically binds to PILRα and inhibits degranulation in mast cell transfectants expressing PILRα (such as DT866) that are stimulated with DX87 (an antibody specific for the activating receptor CD200RLa), as measured by β-hexosaminidase release, is an agonistic anti-PILRα antibody. See U.S. Pat. App. Pub. No. 20030223991, the disclosure of which is hereby incorporated by reference in its entirety. Such data are and particularly reliable if degranulation is inhibited in a concentration-dependent manner.

To determine whether an antibody is a mouse PILRβ antagonist, degranulation is triggered by incubating $1 \times 10^6$ mouse mast cells with a ligand for PILRβ, such as murine CD99, for one hour in RPMI 1640 medium in 96-well plates, in the presence and in the absence of the potential PILRβ antagonist antibody. An antibody that specifically binds to PILRβ and inhibits degranulation in mast cell transfectants expressing PILRβ (such as DT865) that are stimulated with CD99, as measured by β-hexosaminidase release, is an antagonistic anti-PILRβ antibody. Such data are and particularly reliable if degranulation is inhibited in a concentration-dependent manner.

One of skill in the art would recognize that the screening assays described in this example for the identification of antagonists of mouse PILRβ and agonists of mouse PILRα could be adapted for identification of antagonists of human PILRβ and agonists of human PILRα. Specifically, antibodies raised to human forms of PILRβ and PILRα could be screened in a mast cell degranulation assays involving human (rather than mouse) mast cells. Human cell lines or animals could be engineered to express the human CD200R1L, PILRβ and/or PILRα for use in screening. Human CD200R1L, also known as CD200RLa, is an activating form of CD200R and is further described at Gene ID No. 344807 at the NCBI website, and the nucleic acid and polypeptide sequences are provided at RefSeq NM_001008784.2 and NP_001008784.2, respectively.

For identification of human PILRα agonists, an agonist antibody specific for the activating human receptor CD200R1L may be used to stimulate degranulation, rather than DX87. Alternatively, an agonist antibody for human PILRβ, previously selected for its ability to stimulate mast cell degranulation, may be used in place of DX87 to stimulate degranulation in human mast cells expressing both expressing both PILRβ and PILRα.

For identification of human PILRβ antagonists, human CD99 (SEQ ID NOS: 6 and 8) is used in place of mouse CD99-like molecule to stimulate degranulation. See, e.g., Shiratori et al. (2004) *J. Exp. Med.* 199:525 at 532.

Example 3

PILRβ−/− Mice

PILRβ−/− mice were developed to aid in study of the role of PILRβ. A knockout of the PILRβ gene in mice was generated using homologous recombination in mouse embryonic stem cells and subsequent blastocyst injection of the appropriate targeted ES cells to create the gene targeted mice. The mouse chromosome 5 sequence (n.t. #135,226,000135,306,000) was retrieved from the Ensembl database Build 30 and used as reference in this project. BAC clone RP23-131D06 was used for generating homologous arms and southern probes by PCR or RED cloning/gap-repair method. The 5' homologous arm (8.7 kb) was generated by RED cloning/gap repair, and the 3' homologous arm (2.2 kb) was generated by PCR reaction using proofreading LA Taq DNA polymerase (Takara). They were cloned in FtNwCD or pCR4.0 vector and confirmed by restriction digestion and end-sequencing.

The final vector was obtained by standard molecular cloning methods and comprised the homologous arms, the FRT flanked Neo expression cassette (for positive selection of the ES cells), and a DTA expression cassette (for negative selection of the ES cells). The final vector was confirmed by both restriction digestion and end sequencing analysis. NotI was used for linearizing the final vector for electroporation. 3' external probes were generated by PCR reaction using proofreading LA Taq DNA polymerase (Takara) and tested on genomic Southern analysis for ES screening. It was cloned in pCR4.0-TOPO backbone and confirmed by sequencing. The final vector was injected in blastocysts to generate the PILRβ−/− mice. PILRβ−/− were generated on a C57BL/6 background (from Taconic). The resulting knockout founder mice were genotyped. The resulting mice were tested for the absence of the PILRβ gene by analyzing their genetic background by simple sequence length polymorphism. PCR was done using the Taq PCR Master kit (Qiagen).

The phenotype of PILR−/− mice was characterized as follows. The lack of cell surface expression of PILRβ was confirmed by FACS staining mouse leukocytes purified from 6-8 wk old male or female PILR−/− mice and their corresponding C57BL/6J age-matched WT controls. Cells were purified as described above and incubated with anti-mPILRβ, anti-mPILRα or anti-mPILRα/β monoclonal antibodies for 1 h at 4 deg C. Cells were washed twice in staining buffer and further incubated for 30 minutes with PE-conjugated goat anti-rat secondary antibody. Cells were washed and the cell surface expression of PILRα/β in wt and PILRβ−/− mice was determined by flow cytometric analysis using a FACScalibur, (BD Biosciences, Mountain View, Calif.). A complete blood count was also obtained for these mice using the Advia system. In order to evaluate the knockdown of the PILRβ gene at the mRNA and protein levels, various organs such as the heart, lung, liver, kidney and spleen were harvested and submitted for RT-PCR analysis and immunohistochemistry, respectively. For a cell differential analysis, cells from the bone marrow and erythrocyte-depleted splenocytes were labeled with PE-conjugated anti-GR-1, anti-ClassII, anti-CD3 and anti-NK1.1; FITC-conjugated anti-CD45, anti-CD11c, anti-CD8 and anti-CD25; APC-conjugated anti-CD11b, anti-B220 and anti-CD4 (all from BD Biosciences).

PILR−/− mice were bred as homozygous knockouts and wild-type (WT) C57Bl/6 (Jackson Laboratories, Bar Harbor, Me.) were used as age- and sex-matched controls in all experiments. All animal procedures were approved by the Institutional Animal Care and Use Committee of Schering-Plough Biopharma in accordance with guidelines of the Association for Assessment and Accreditation of Laboratory Animal Care.

Example 4

Mouse Disease Models

Exemplary mouse models of human inflammatory disorders are described generally as follows, and as described in greater detail in subsequent Examples herein.

A first mouse model of multiple sclerosis (CNS inflammation), based on administration of CFA and pertussis toxin, was used in experiments involving agonist anti-PILR antibodies. See, e.g., Kamradt et al. (1991) *J. Immunol.* 147:3296, the disclosure of which is hereby incorporated by reference in its entirety. See also Examples 5 and 6 herein.

A mouse model of rheumatoid arthritis based on administration of Chemicon's arthrogen CIA cocktail (i.e. the CAIA model) is described at, e.g., Khachigian (2006) *Nat. Protocols* 1:2512. See also, e.g., U.S. Pat. App. Pub. No. 2007/0036750; Nandakumar & Holmdahl (2007) *Methods Mol. Med.* 136:215. See also Example 6 herein.

A mouse model of IBD based on per-oral administration of *T. gondii* was used, e.g., as described at Kasper et al. (2004) *Int. J. Parasitol.* 34:401 and Liesenfeld (2002) *J. Infect. Dis.* 185 Suppl 1:S96-101, the disclosures of which are hereby incorporated by reference in their entireties. See also Example 7 herein.

A second mouse model of multiple sclerosis (CNS inflammation), based on peritoneal administration of *T. gondii*, was used in experiments involving PILRβ−/− mice. See, e.g., Wilson & Hunter (2004) *Int. J. Parasitol.* 34:543, the disclo- Example 5

An FDF03 Bi-Specific Antibody Inhibits EAE

To explore the effects of activation of PILRα and PILRβ on EAE, SJL mice were immunized with 100 μg PLP-139-151 in complete Freund's adjuvant (CFA), and given 100 ng pertussis toxin on day 0 and day 2 post-immunization. Animals were then treated with 0.5 mg of IgG1 control or DX173 on days 3, 6, and 9 post-immunization. Weight and disease score were monitored for 40 days. EAE clinical score is based on the following system: 1=limp tail, 2=hind leg weakness, 3=partial hind limb paralysis, 4=complete hind limb paralysis, 5=moribund. The results shown in FIG. 1 demonstrate that FDF03 bi-specific antibody (DX173) inhibits experimental autoimmune encephalomyelitis (EAE). Although some evidence of disease is visible in DX173-treated animals, disease severity is dramatically reduced.

Further experiments were performed to examine the effect of DX173 on T cell proliferation. EAE was induced in SJL mice using 100 μg PLP 139-151 in CFA and 100 ng pertussis toxin. Mice were treated on days 3 and 6 after disease induction with 0.5 mg of DX173 or IgG1 isotype control. Lymph node cells from each group (day 7 after disease induction) were cultured for 48 hours with or without the immunizing peptide The results shown in FIG. 2A demonstrate that DX173 significantly reduces antigen-specific T cell proliferation.

Still further experiments were performed to determine the mechanism by which DX173 inhibits T cell proliferation. EAE SJL mice were treated with antibodies as described in the preceding paragraph. Lymph node cells from each group were sorted for CD 11c and CD4 using Miltenyi Biotec's autoMACS cell sorter to separate and isolate dendritic cells (DCs) and T cells. The result was four purified populations of cells, comprising DC's and T cells from either isotype or DX173-treated cells. All pairwise combinations of DCs and T cells were co-cultured in the presence of absence of varying concentration of immunizing peptide. In all cultures, DCs were added at a 1:20 ratio to T cells. Immunizing peptide was titrated into cultures and tritium incorporation (CPM) was measured at 48 hours. The results, shown in FIG. 2B, demonstrate that DX173 inhibits dendritic cells' ability to stimulate T-cell proliferation.

Example 6

An Anti-FDF03inhib/PILRα Antibody Inhibits EAE and CAIA

Experiments were performed to determine which form(s) of FDF03 (activating, inhibitory, or both) was responsible for EAE results obtained with the bispecific antibody DX173. SJL mice were induced with 100 μg PLP 139-151 in CFA and 100 ng pertussis toxin to induce EAE. These EAE mice were treated with 0.5 mg of either IgG1 isotype control antibody or DX276 (an agonist antibody specific for FDF03inhib/PILRα) on days 3, 6, and 9.

A further experiment was performed to explore the effects of FDF03 inhibition in collagen antibody-induced arthritis (CAIA), a model of human rheumatoid arthritis. B10 RIII mice (n=5 per group) were given 1000 μg of Chemicon's arthrogen CIA cocktail (Chemicon Inc., Temecula, Calif., USA) intravenously to induce CAIA on Day 0. Mice were subsequently given a subcutaneous 0.5 mg dose of IgG1 isotype control antibody or FDF03 activating (DX266), FDF03 inhibitory (DX276), or bi-specific (DX173) antibody on days 0 and 2. Clinical score is based on paw swelling per foot. Score 1=1 toe, 2=two or more toes; 3=entire paw swelling. Maximum clinical score per mouse is 12.

The results demonstrate that FDF03 inhibitory antibody (DX276) inhibits both EAE (FIG. 3A) and CAIA (FIG. 3B). Comparison of the effects of antibodies DX266, DX276 and DX173 in the CAIA model (FIG. 3B) reveals that binding to the inhibitory form of FDF03 (PILRα) is most protective, with the bispecific antibody being somewhat less effective, and the antibody to the activating form of the receptor being least effective (although still decreasing disease as compared to isotype control. These results suggest that the protective effects observed with bispecific antibody DX173 are predominantly the result of its binding to the inhibitory, rather than the activating, form of FDF03.

Example 7

PILRβ−/− Mice Exhibit Enhanced Survival in a Model Inflammatory Bowel Disease

To examine the effects of altering FDF03/PILR signaling on inflammatory bowel disease (IBD), PILRβ−/− and WT mice were used in a model involving per-oral infection with high dose *Toxoplasma gondii*. Such mice are referred to herein as "IBD mice." This model of infection mimics the immunological and histological mechanisms associated with human IBD pathology, including CD4+T cell mediated damage to the epithelium that can be modulated by IL-10. Upon infection, WT C57Bl/6 mice normally succumb by day 7-14. Susceptibility is associated with an uncontrolled inflammatory response in the small intestine that causes severe epithelial damage. Mice were infected with 80-100 cysts of Me-49 strain of *T. gondii* and observed for survival.

Experiments were performed to determine which cytokines were responsible for mediating the increased IBD resistance of PILRβ−/− mice. Sections of ileum were removed from mice 10 days after either per oral PBS or parasite (*T. gondii*) challenge, fixed in 10% NBF, and embedded in paraffin. Sections were H&E stained to visualize epithelial tissue and inflammatory infiltrate, and analysis of WT ileum revealed the presence of more cellular infiltrate in the lamina propria and more blood compared to PILRβ−/− sections at the same time point, and was indicative of severe breakdown of the epithelial border and enhanced barrier permeability (data not shown). Additionally, spleens were harvested at day 7 (FIGS. 5A and 5C) or day 10 (FIGS. 5B and 5D) post challenge and cultured in recall assays for 3 days before analyzing for the presence of cytokine by ELISA. Protein content was quantified using ELISA kits for IFNγ (R&D Systems, Minneapolis, Minn., USA) and IL-10 (Invitrogen, Carlsbad, Calif., USA). Results show significantly more IFNγ production in response to soluble *Toxoplasma* antigen (STAg) or αCD3 restimulation, along with enhanced IL-10 production by T cells, at day 7 (FIGS. 5A and 5C). Furthermore, both T cell and antigen specific production of IL-10 were maintained at significantly higher levels at day 10 (FIG. 5D). By day 10 splenocyte cultures exhibited no difference in IFNγ production between strains (FIG. 5B).

To determine whether IL-27 was involved in mediating the phenotype of PILRβ−/− mice, production of IL-27p28 in WT and PILRβ−/− mice was assessed by p28 ELISA in IBD mice. Serum levels of IL-27p28 were increased by day 7 in the PILRβ−/− mice compared to WT (FIG. 6A), and this trend of higher p28 production in the KO mice was maintained through day 10 and 14 after per oral challenge (FIG. 6B). All p values<0.032. Collectively, FIGS. 6A and 6B show that IL-27p28 production is increased after infection, and is increased to a greater extent in PILRβ−/− mice than in WT mice.

In addition, recall assays using mesenteric lymph nodes were performed. Draining lymph nodes were removed at day 5 post-challenge and cultured in recall assays for 3 days, before analyzing IL-27p28 levels in the supernatant by ELISA. Protein content was quantified using an ELISA kit for IL-27p28 (R&D Systems, Minneapolis, Minn., USA). As shown in FIG. 6C, significantly higher levels of p28 protein were present in response to STAg and in response to αCD3 stimulation.

Because it was only possible to detect p28 protein in serum and supernatant samples, minicircle experiments were performed to determine which component of IL-27, or the IL-27 heterodimer complex itself, was responsible for the observed resistance to IBD in PILRβ−/− mice. Expression of p28, EBi3, IL-27 hyperkine, or eGFP control were induced in C57Bl/6 mice in vivo using minicircle DNA for systemic expression of each 4 days before high dose per-oral infection with $T.$ gondii. Minicircle DNA vectors for p28, EBi3, IL-27 hyperkine and eGFP transgenes were prepared using a phage ϕc31 integrase-mediated intramolecular recombination strategy as previously described (37). Minicircles were then administered using a hydrodynamics-based transfection procedure as described previously (38). Systemic expression of specific transgenes was verified using ELISA to analyze peripheral blood at various time points. Survival curves of all groups through 14 days post infection are presented at FIG. 7A. Mortality after challenge occurred in all control groups beginning at day 8 post-infection other than the IL-27-expressing group, suggesting a requirement for IL-27, and not p28 alone, to mediate resistance.

Figure 7D:
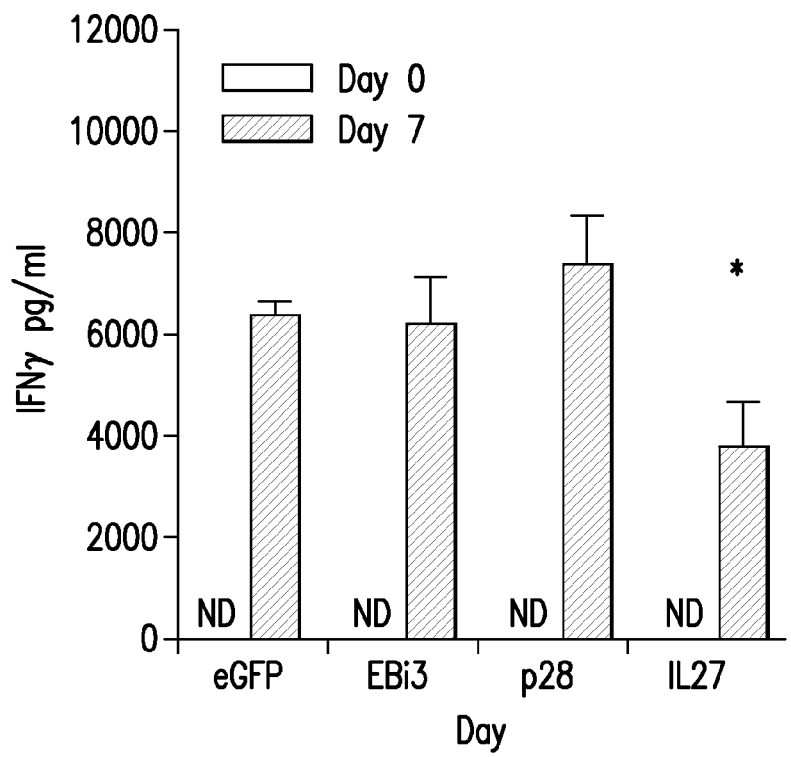

Serum cytokine levels were also monitored by ELISA at day 0 (IL-27p28 only) and day 5 post infection. Protein content was quantified using ELISA kits for IFNγ and IL-27p28 (R&D Systems, Minneapolis, Minn., USA) and IL-10 (Invitrogen, Carlsbad, Calif., USA). Not surprisingly, significantly high levels of IL-27p28 were observed in both groups that were injected with IL-27 and p28 expressing minicircles (FIG. 7B). Enhanced IL-10 production was evident in IL-27-expressing mice, but not in p28-expressing or control mice (FIG. 7C). INFγ at day 5 was significantly reduced compared to eGFP control mice (FIG. 7D).

Example 8

PILRβ−/− Mice Exhibit Enhanced Survival in a Mouse Model of CNS Inflammation

To examine the effects of altering FDF03/PILR signaling on multiple sclerosis and CNS inflammation generally, PILRβ−/− and WT mice were used in an immune-mediated encephalitis model involving intra-peritoneal (i.p.) administration of $T.$ gondii. Such mice are referred to herein as "encephalitis mice."

WT and PILRβ−/− C57BL/6 mice were infected with 20 cysts Me-49 i.p. and followed out to 100 days post infection. mRNA for the inhibitory receptor (FIG. 8A, left panel) and the activating receptor (FIG. 8A, right panel) is expressed in brain mononuclear cells (BMNCs) isolated from the CNS of WT or PILRβ−/− mice 60-90 days post infection, with the (expected) exception that no activating receptor (PILRβ) message was detected in PILRβ−/− BMNCs. Serum protein levels of IL-27p28 were analyzed in samples from either acutely or chronically infected mice (FIGS. 8B and 8C, respectively). Serum IL-27p28 was significantly higher in PILRβ−/− than in WT mice at both time points. PILRβ−/− mice exhibited increased survival compared with WT mice (FIG. 8D).

Brain samples were also inspected for effects of PILRβ deficiency. Brain sections were fixed in 10% NBF before embedding in paraffin. Histology after H&E staining of brain sections from WT and PILRβ−/− encephalitis mice at approximately day 60 post infection revealed increased numbers of inflammatory foci in WT mice compared to PILRβ−/− mice (data not shown). In addition, parasite burden was determined by counting the number of cysts present in brain homogenate from chronically infected WT and PILRβ−/− mice 60-90 days post infection (FIG. 9A). To count cysts, individual brains from chronically infected mice were processed in 3 ml of PBS using syringes and consecutive 18G, 20G and 22G needles to create a homogenate. The number of cysts present in 30 μl of homogenate was used to determine the total number of cysts present within each brain. Cellular infiltrate during chronic infection was also quantified after isolating BMNCs from whole brains from WT and PILRβ−/− and encephalitis mice 60-90 days post infection (FIG. 9B). Both cyst count and cellular infiltrate demonstrate that PILRβ−/− mice are resistant to $T.$ gondii-induced CNS inflammation.

IFNγ and IL-10 levels were then determined in recall assays with BMNCs isolated from brains of WT and PILRβ−/− encephalitis mice (FIGS. 9C and 9D). Cells were cultured for three days in recall assays in the presence of media alone, STAg, or αCD3. Protein content was quantified using ELISA kits for IFNγ (R&D Systems, Minneapolis, Minn., USA) or IL-10 (Invitrogen, Carlsbad, Calif., USA). The results show greater T cell production of IFNγ and IL-10 in PILRβ−/− mice than in WT mice after restimulation with either STAg or αCD3.

Example 9

PILRβ−/− Splenic DCs and Macrophages Exhibit a More "Tolerogenic" Phenotype

Experiments were performed to determine whether APCs from PILRβ−/− encephalitis mice exhibit a more "tolerogenic" phenotype than WT cells. WT and PILRβ−/− mice were infected with $T.$ gondii i.p., and on day 5 DCs and macrophages were sorted from individual spleens. Sorted populations were then analyzed for mRNA levels of various proteins by RT-PCR. The results are presented in FIGS. 10A-10E. Similar levels of PILRα were present on DCs and macrophages isolated from WT (white bars) and PILRβ−/− (black bars) mice (FIG. 10A). However, message levels of IL-10 (FIG. 10B), TNFα (FIG. 10C), and IL-6 (FIG. 10D) were increased in PILRβ−/− DCs compared to WT DCs. MIP2, a proinflammatory chemokine produced by macrophages, was dramatically reduced in macrophages from PILRβ−/− mice compared to WT (FIG. 10E).

Sorted day 5 DCs and macrophages from WT and PILRβ−/− encephalitis mice were also cultured overnight in the presence of plate-bound antibody for the activating or the inhibitory receptor or control Ig, followed by ELISA analysis of the cell supernatant for the presence of MIP2. WT macrophages produced higher levels of MIP2 protein when stimulated with STAg in the presence of antibody for the activating receptor (PILRβ) than in the presence of antibodies for the inhibitory receptor (PILRα) (FIG. 10F, left half).

PILRβ deficient macrophages produced significantly less MIP2 than WT in response to either STAg or LPS (FIG. 10F, right half).

IL-10 and IFN-γ were then detected by intracellular staining of CD4+T cells stimulated by either DCs of macrophages from WT or PILRβ−/− mice. DCs and macrophages were isolated from infected naïve WT and PILRβ−/− (encephalitis) mice 5 days post-infection, pulsed with OVA-peptide for 3 hours at 37° C., and co-cultured with OTII Tg T cells (also Macs-sorted for CD4+ T cells) for 3 days. Intracellular cytokine staining was performed to determine capacity for cytokine production, and as a read out of activation. FIG. 10G provides dot plots for T cells stimulated by DCs (left panels) or macrophages (right panels) and show IL-10 versus IFNγ staining of gated CD4+ T cells. Percentages of CD4 gate are shown in each quadrant. PILRβ−/− DCs or macrophages induced fewer IFNγ+ T cells and more IL-10+ cells.

VI. References

1. Turnbull et al., I. R., and M. Colonna. 2007. Activating and inhibitory functions of DAP12. Nat Rev Immunol 7:155-161.
2. Mousseau, D. D., D. Banville, D. L'Abbe, P. Bouchard, and S. H. Shen. 2000. PILRalpha, a novel immunoreceptor tyrosine-based inhibitory motif-bearing protein, recruits SHP-1 upon tyrosine phosphorylation and is paired with the truncated counterpart PILRbeta. J Biol Chem 275: 4467-4474.
3. Fournier, N., L. Chalus, I. Durand, E. Garcia, J. J. Pin, T. Churakova, S. Patel, C. Zlot, D. Gorman, S. Zurawski, J. Abrams, E. E. Bates, and P. Garrone. 2000. FDF03, a novel inhibitory receptor of the immunoglobulin superfamily, is expressed by human dendritic and myeloid cells. J Immunol 165:1197-1209.
4. Shiratori, I., K. Ogasawara, T. Saito, L. L. Lanier, and H. Arase. 2004. Activation of natural killer cells and dendritic cells upon recognition of a novel CD99-like ligand by paired immunoglobulin-like type 2 receptor. J Exp Med 199:525-533.
5. Tabata, S., K. Kuroki, J. Wang, M. Kajikawa, I. Shiratori, D. Kohda, H. Arase, and K. Maenaka. 2008. Biophysical characterization of O-glycosylated CD99 recognition by paired Ig-like type 2 receptors. J Biol Chem 283:8893-8901.
6. Wang, J., I. Shiratori, T. Satoh, L. L. Lanier, and H. Arase. 2008. An essential role of sialylated O-linked sugar chains in the recognition of mouse CD99 by paired Ig-like type 2 receptor (PILR). J Immunol 180:1686-1693.
7. Oh, K. I., B. K. Kim, Y. L. Ban, E. Y. Choi, K. C. Jung, I. S. Lee, and S. H. Park. 2007. CD99 activates T cells via a costimulatory function that promotes raft association of TCR complex and tyrosine phosphorylation of TCR zeta. Exp Mol Med 39:176-184.
8. Bixel, M. G., B. Petri, A. G. Khandoga, A. Khandoga, K. Wolburg-Buchholz, H. Wolburg, S. Marz, F. Krombach, and D. Vestweber. 2007. A CD99-related antigen on endothelial cells mediates neutrophil but not lymphocyte extravasation in vivo. Blood 109:5327-5336.
9. Lou, O., P. Alcaide, F. W. Luscinskas, and W. A. Muller. 2007. CD99 is a key mediator of the transendothelial migration of neutrophils. J Immunol 178:1136-1143.
10. Dufour, E. M., A. Deroche, Y. Bae, and W. A. Muller. 2008. CD99 is essential for leukocyte diapedesis in vivo. Cell Commun Adhes 15:351-363.
11. Satoh, T., and H. Arase. 2008. HSV-1 infection through inhibitory receptor, PILRalpha. Uirusu 58:27-36.
12. Satoh, T., J. Arii, T. Suenaga, J. Wang, A. Kogure, J. Uehori, N. Arase, I. Shiratori, S. Tanaka, Y. Kawaguchi, P. G. Spear, L. L. Lanier, and H. Arase. 2008. PILRalpha is a herpes simplex virus-1 entry coreceptor that associates with glycoprotein B. Cell 132:935-944.
13. Liesenfeld, O. 2002. Oral infection of C57BL/6 mice with *Toxoplasma gondii*: a new model of inflammatory bowel disease? J Infect Dis 185 Suppl 1:S96-101.
14. Suzuki, Y., A. Sher, G. Yap, D. Park, L. E. Neyer, O. Liesenfeld, M. Fort, H. Kang, and E. Gufwoli. 2000. IL-10 is required for prevention of necrosis in the small intestine and mortality in both genetically resistant BALB/c and susceptible C57BL/6 mice following peroral infection with *Toxoplasma gondii*. J Immunol 164:5375-5382.
15. Stumhofer, J. S., J. S. Silver, A. Laurence, P. M. Porrett, T. H. Harris, L. A. Turka, M. Ernst, C. J. Saris, J. J. O'Shea, and C. A. Hunter. 2007. Interleukins 27 and 6 induce STAT3-mediated T cell production of interleukin 10. Nat Immunol 8:1363-1371.
16. Villarino, A., L. Hibbert, L. Lieberman, E. Wilson, T. Mak, H. Yoshida, R. A. Kastelein, C. Saris, and C. A. Hunter. 2003. The IL-27R (WSX-1) is required to suppress T cell hyperactivity during infection. Immunity 19:645-655.
17. Troy, A. E., C. Zaph, Y. Du, B. C. Taylor, K. J. Guild, C. A. Hunter, C. J. Saris, and D. Artis. 2009. IL-27 regulates homeostasis of the intestinal CD4+ effector T cell pool and limits intestinal inflammation in a murine model of colitis. J Immunol 183:2037-2044.
18. Murugaiyan, G., A. Mittal, R. Lopez-Diego, L. M. Maier, D. E. Anderson, and H. L. Weiner. 2009. IL-27 is a key regulator of IL-10 and IL-17 production by human CD4+ T cells. J Immunol 183:2435-2443.
19. Ilarregui, J. M., D. O. Croci, G. A. Bianco, M. A. Toscano, M. Salatino, M. E. Vermeulen, J. R. Geffner, and G. A. Rabinovich. 2009. Tolerogenic signals delivered by dendritic cells to T cells through a galectin-1-driven immunoregulatory circuit involving interleukin 27 and interleukin 10. Nat Immunol 10:981-991.
20. Tait, E. D., and C. A. Hunter. 2009. Advances in understanding immunity to *Toxoplasma gondii*. Mem Inst Oswaldo Cruz 104:201-210.
21. Stumhofer, J. S., and C. A. Hunter. 2008. Advances in understanding the anti-inflammatory properties of IL-27. Immunol Lett 117:123-130.
22. Villarino, A. V., J. S. Stumhofer, C. J. Saris, R. A. Kastelein, F. J. de Sauvage, and C. A. Hunter. 2006. IL-27 limits IL-2 production during Th1 differentiation. J Immunol 176:237-247.
23. Stumhofer, J. S., A. Laurence, E. H. Wilson, E. Huang, C. M. Tato, L. M. Johnson, A. V. Villarino, Q. Huang, A. Yoshimura, D. Sehy, C. J. Saris, J. J. O'Shea, L. Hennighausen, M. Ernst, and C. A. Hunter. 2006. Interleukin 27 negatively regulates the development of interleukin 17-producing T helper cells during chronic inflammation of the central nervous system. Nat Immunol 7:937-945.
24. Artis, D., A. Villarino, M. Silverman, W. He, E. M. Thornton, S. Mu, S. Summer, T. M. Covey, E. Huang, H. Yoshida, G. Koretzky, M. Goldschmidt, G. D. Wu, F. de Sauvage, H. R. Miller, C. J. Saris, P. Scott, and C. A. Hunter. 2004. The IL-27 receptor (WSX-1) is an inhibitor of innate and adaptive elements of type 2 immunity. J Immunol 173:5626-5634.
25. L1, J., B. Gran, G. X. Zhang, A. Rostami, and M. Kamoun. 2005. IL-27 subunits and its receptor (WSX-1) mRNAs are markedly up-regulated in inflammatory cells in the CNS during experimental autoimmune encephalomyelitis. J Neurol Sci 232:3-9.

26. Sonobe, Y., I. Yawata, J. Kawanokuchi, H. Takeuchi, T. Mizuno, and A. Suzumura. 2005. Production of IL-27 and other IL-12 family cytokines by microglia and their subpopulations. Brain Res 1040:202-207.
27. Fitzgerald, D. C., B. Ciric, T. Touil, H. Harle, J. Grammatikopolou, J. Das Sarma, B. Gran, G. X. Zhang, and A. Rostami. 2007. Suppressive effect of IL-27 on encephalitogenic Th17 cells and the effector phase of experimental autoimmune encephalomyelitis. J Immunol 179:3268-3275.
28. Liesenfeld, O., H. Kang, D. Park, T. A. Nguyen, C. V. Parkhe, H. Watanabe, T. Abo, A. Sher, J. S. Remington, and Y. Suzuki. 1999. TNF-alpha, nitric oxide and IFN-gamma are all critical for development of necrosis in the small intestine and early mortality in genetically susceptible mice infected perorally with *Toxoplasma gondii*. Parasite Immunol 21:365-376.
29. Liesenfeld, O., J. Kosek, J. S. Remington, and Y. Suzuki. 1996. Association of CD4+ T cell-dependent, interferon-gamma-mediated necrosis of the small intestine with genetic susceptibility of mice to peroral infection with *Toxoplasma gondii*. J Exp Med 184:597-607.
30. Jankovic, D., M. C. Kullberg, C. G. Feng, R. S. Goldszmid, C. M. Collazo, M. Wilson, T. A. Wynn, M. Kamanaka, R. A. Flavell, and A. Sher. 2007. Conventional T-bet(+)Foxp3(−) Th1 cells are the major source of host-protective regulatory IL-10 during intracellular protozoan infection. J Exp Med 204:273-283.
31. Niedbala, W., B. Cai, X. Wei, A. Patakas, B. P. Leung, I. B. McInnes, and F. Y. Liew. 2008. Interleukin 27 attenuates collagen-induced arthritis Ann Rheum Dis 67:1474-1479.
32. Fitzgerald, D. C., G. X. Zhang, M. El-Behi, Z. Fonseca-Kelly, H. Li, S. Yu, C. J. Saris, B. Gran, B. Ciric, and A. Rostami. 2007. Suppression of autoimmune inflammation of the central nervous system by interleukin 10 secreted by interleukin 27-stimulated T cells. Nat Immunol 8:1372-1379.
33. Furuzawa-Carballeda, J., M. I. Vargas-Rojas, and A. R. Cabral. 2007. Autoimmune inflammation from the Th17 perspective. Autoimmun Rev 6:169-175.
34. Diveu, C., M. J. McGeachy, K. Boniface, J. S. Stumhofer, M. Sathe, B. Joyce-Shaikh, Y. Chen, C. M. Tato, T. K. McClanahan, R. de Waal Malefyt, C. A. Hunter, D. J. Cua, and R. A. Kastelein. 2009. IL-27 blocks RORc expression to inhibit lineage commitment of Th17 cells. J Immunol 182:5748-5756.
35. Cua, D. J., J. Sherlock, Y. Chen, C. A. Murphy, B. Joyce, B. Seymour, L. Lucian, W. To, S. Kwan, T. Churakova, S. Zurawski, M. Wiekowski, S. A. Lira, D. Gorman, R. A. Kastelein, and J. D. Sedgwick. 2003. Interleukin-23 rather than interleukin-12 is the critical cytokine for autoimmune inflammation of the brain. Nature 421:744-748.
36. Langrish, C. L., Y. Chen, W. M. Blumenschein, J. Mattson, B. Basham, J. D. Sedgwick, T. McClanahan, R. A. Kastelein, and D. J. Cua. 2005. IL-23 drives a pathogenic T cell population that induces autoimmune inflammation. J Exp Med 201:233-240.
37. Chen, Z. Y., C. Y. He, A. Ehrhardt, and M. A. Kay. 2003. Minicircle DNA vectors devoid of bacterial DNA result in persistent and high-level transgene expression in vivo. Mol Ther 8:495-500.
38. Liu, F., Y. Song, and D. Liu. 1999. Hydrodynamics-based transfection in animals by systemic administration of plasmid DNA. Gene Ther 6:1258-1266.
39. Fehniger, T. A., M. H. Shah, M. J. Turner, J. B. VanDeusen, S. P. Whitman, M. A. Cooper, K. Suzuki, M. Wechser, F. Goodsaid, and M. A. Caligiuri. 1999. Differential cytokine and chemokine gene expression by human NK cells following activation with IL-18 or IL-15 in combination with IL-12: implications for the innate immune response. J Immunol 162:4511-4520.

TABLE 2

| SEQ ID NO: | Description | RefSeq |
|---|---|---|
| 1 | human PILRα nucleic acid | NM_013439.2 |
| 2 | human PILRα polypeptide | NP_038467.2 |
| 3 | human PILRβ nucleic acid | NM_013440.3 |
| 4 | human PILRβ polypeptide | NP_038468.3 |
| 5 | human CD99 (long isoform) nucleic acid | NM_002414.3 |
| 6 | human CD99 (long isoform) polypeptide | NP_002405.1 |
| 7 | human CD99 (short isoform) nucleic acid | NM_001122898.1 |
| 8 | human CD99 (short isoform) polypeptide | NP_001116370.1 |

What is claimed is:

1. A method of treating an immune disorder selected from the list consisting of multiple sclerosis, rheumatoid arthritis and inflammatory bowel disease, comprising administering to a subject in need of such treatment an effective amount of an antigen-binding domain from an agonist antibody that specifically binds to PILRα (SEQ ID NO: 2).

2. The method of claim 1 comprising administering an effective amount of an agonist antibody that specifically binds to PILRα.

3. The method of claim 2 wherein the agonist antibody that specifically binds to PILRα is a chimeric, humanized, or fully human antibody.

4. The method of claim 1, wherein the immune disorder is multiple sclerosis.

5. The method of claim 1, wherein the immune disorder is inflammatory bowel disease.

6. The method of claim 1, wherein the immune disorder is rheumatoid arthritis.

* * * * *